(12) United States Patent
Schäfer

(10) Patent No.: US 8,946,129 B2
(45) Date of Patent: Feb. 3, 2015

(54) MASS LABELS

(75) Inventor: Jürgen Schäfer, Lauterbach (DE)

(73) Assignee: Electrophoretics Limited, Cobham, Surrey (GB)

( * ) Notice: Subject to any disclaimer, the term of this patent is extended or adjusted under 35 U.S.C. 154(b) by 1620 days.

(21) Appl. No.: 12/066,584

(22) PCT Filed: Sep. 11, 2006

(86) PCT No.: PCT/GB2006/003341
§ 371 (c)(1),
(2), (4) Date: Oct. 14, 2009

(87) PCT Pub. No.: WO2007/031717
PCT Pub. Date: Mar. 22, 2007

(65) Prior Publication Data
US 2010/0029495 A1    Feb. 4, 2010

(30) Foreign Application Priority Data

Sep. 12, 2005    (GB) .................................. 0518585.5

(51) Int. Cl.
| | |
|---|---|
| C40B 70/00 | (2006.01) |
| C40B 20/04 | (2006.01) |
| G01N 33/532 | (2006.01) |
| G01N 33/68 | (2006.01) |
| C07B 59/00 | (2006.01) |

(52) U.S. Cl.
CPC .......... *G01N 33/532* (2013.01); *G01N 33/6851* (2013.01); *C12Q 2563/167* (2013.01)
USPC .................. 506/41; 506/4; 436/173

(58) Field of Classification Search
CPC .... G01N 2458/15; C40B 20/04; C40B 70/00; C07B 59/00
USPC ......................................... 506/4, 41
See application file for complete search history.

(56) References Cited

U.S. PATENT DOCUMENTS

| | | | |
|---|---|---|---|
| 2005/0042625 A1 | 2/2005 | Schmidt et al. | |
| 2007/0207555 A1* | 9/2007 | Guerra et al. | .................. 436/518 |

FOREIGN PATENT DOCUMENTS

| | | |
|---|---|---|
| WO | 9504160 A1 | 2/1995 |
| WO | 9727325 A2 | 7/1997 |
| WO | 9727327 A2 | 7/1997 |

(Continued)

OTHER PUBLICATIONS

Klassen et al., J. Amer. Chem. Soc., 1997, 119:6552-6563.*

(Continued)

*Primary Examiner* — Christopher M Babic
*Assistant Examiner* — Jeremy C Flinders
(74) *Attorney, Agent, or Firm* — Arent Fox LLP

(57) ABSTRACT

Provided is a set of mass labels, each mass label in the set comprising a mass marker moiety attached via a cleavable linker to a mass normalization moiety, each mass label in the set having a common mass; wherein the set comprises a plurality of groups of mass labels, the mass of the mass marker moiety being the same for mass labels within a group, the mass of the mass marker moiety being different between groups; the mass marker moiety is capable of fragmentation into two or three fragments; and the mass of at least one fragment of the mass marker moiety differs between mass labels within a group.

36 Claims, 6 Drawing Sheets

(56) References Cited

FOREIGN PATENT DOCUMENTS

| WO | 9727331 A2 | 7/1997 |
|---|---|---|
| WO | 9826096 A1 | 6/1998 |
| WO | 9832876 A1 | 7/1998 |
| WO | WO 98/31830 | 7/1998 |
| WO | 9932501 A1 | 7/1999 |
| WO | 00/02893 A1 | 1/2000 |
| WO | 0002895 A1 | 1/2000 |
| WO | 0020870 A1 | 4/2000 |
| WO | WO 01/68664 | 9/2001 |
| WO | 02099435 A1 | 12/2002 |
| WO | WO 03/025576 | 3/2003 |
| WO | 03087839 A1 | 10/2003 |
| WO | 2005012914 A2 | 2/2005 |

OTHER PUBLICATIONS

Gygi, S.P., et al., "Quantitative analysis of complex protein mixtures using isotope-coded affinity tags", Nature America Inc., Nature Biotechnology, vol. 17, Oct. 1999, pp. 994-999.

Maskos; U. et al.; "Oligonucleotide hybridisations on glass supports: a novel linker for oligonucleotide synthesis and hybridisation properties of oligonucleotides synthesised in situ", Nucleic Acids Research, vol. 20, No. 7, Mar. 1992, pp. 1679-1684.

Lloyd-Williams, P. at al., "Convergent Solid-Phase Peptide Synthesis", Tetrahedron, vol. 49, No. 48, 1993, pp. 11065-11133.

Stetter, D., et al., "Preparation of a series of aryl ether carboxylic acids", Institute of Chemistry, University of Bonn, Sep. 21, 1954, pp. 1699-1703.

Iyoda, M. at al., "Synthesis of Riccardin B by Nickel-Catalyzed Intramolecular Cyclization", Tetrahedron Letters, vol. 26, No. 39, 1985, pp. 4777-4780.

Evans, D.A., et al., "Synthesis of Diaryl Ethers through the Copper-Promoted Arylation of Phenols with Arylboronic Acids. An Expedient Synthesis of Thyroxine", Tetrahedron Letters 39, 1998, pp. 2937-2940.

Geahlen, R.L. at al., "A General Method for Preparation of Peptides Biotinylated at the Carboxy Terminus", Analytical Biochemistry, vol. 202, 1992, pp. 68-70.

Sawutz, D.G. at al., "Synthesis and Molecular Characterization of a Biotinylated Analog of [Lys]Bradykinin". Peptides, vol. 12, 1991, pp. 1019-1024.

Natarajan, S. at al., "Site-Specific Biotinylation; a Novel Approach and its Application to Endothelin-1 Analogs and PTH-Analog", Int. J. Peptide Protein Res., vol. 40, 1992, pp. 567-574.

Stolowitz, M.L., at al.; "Phenylboronic Acid-Salicylhydroxamic Acid Bioconjugates. 1. A Novel Boronic Acid Complex for Protein Immobilization", Bioconjugate Chem., vol. 12, No. 2, 2001, pp. 229-239.

Wiley, J.P., et al., "Phenylboronic Acid-Salicylhydroxamic Acid Bioconjugates. 2. Polyvalent Immobilization of Protein Ligands for Affinity Chromatography", Bioconjugate Chem. vol. 12, No. 2, 2001, pp. 240-250.

Bian, N., et al., "Detection Via Laser Desorption and Mass Spectrometry of Multiplex Electrophore-labeled Albumin", Rapid Communications in Mass Spectrometry, vol. 11, Sep. 8, 1997, pp. 1781-1784.

Abdel-Baky, S., et al., "Gas Chromatography/Electron Capture Negative-Ion Mass Spectrometry at the Zeptomole Level", American Chemical Society, Analytical Chemistry, vol. 63, No. 24, Dec. 15, 1991, pp. 2986-2989.

Roth, Mass K.D.W., et al., "Charge Derivatization of Peptides for Analysis by Mass Spectrometry", John Wiley & Sons, Ltd., Mass Spectrometry Reviews, vol. 17, 1998, pp. 255-274.

Wilm, M., et al. "Parent Ion Scans of Unseparated Peptide Mixtures", Analytical Chemistry, vol. 68, No. 3, Feb. 1, 1996, pp. 527-533.

Shevchenko, A. et al., "Rapid 'de Novo' Peptide Sequencing by a Combination of Nanoelectrospray, Isotopic Labeling and a Quadrupole/Time-of-flight Mass Spectrometer", Rapid Communications in Mass Spectrometry, vol. 11, 1997, pp. 1015-1024.

Iyer, V.R., et al., "The Transcriptional Program in the Response of Human Fibroblasts to Serum", Science, vol. 283, No. 83, Jan. 1, 1999, pp. 83-87.

* cited by examiner

MASS LABELS

The present invention relates to mass labels, and particularly to sets and arrays of such mass labels. The mass labels are useful for labelling analytes, such as nucleic acids, peptides and proteins, for subsequent mass spectrometric analysis.

Various methods of labelling molecules of interest are known in the art, including radioactive atoms, fluorescent dyes, luminescent reagents, electron capture reagents and light absorbing dyes. Each of these labelling systems has features which make it suitable for certain applications and not others. For reasons of safety, interest in non-radioactive labelling systems lead to the widespread commercial development of fluorescent labelling schemes particularly for genetic analysis. Fluorescent labelling schemes permit the labelling of a relatively small number of molecules simultaneously, typically 4 labels can be used simultaneously and possibly up to eight. However the costs of the detection apparatus and the difficulties of analysing the resultant signals limit the number of labels that can be used simultaneously in a fluorescence detection scheme.

More recently there has been development in the area of mass spectrometry as a method of detecting labels that are cleavably attached to their associated molecule of interest. In many molecular biology applications one needs to be able to perform separations of the molecules of interest prior to analysis. These are generally liquid phase separations. Mass spectrometry in recent years has developed a number of interfaces for liquid phase separations which make mass spectrometry particularly effective as a detection system for these kinds of applications. Until recently Liquid Chromatography Mass Spectrometry was used to detect analyte ions or their fragment ions directly, however for many applications such as nucleic acid analysis, the structure of the analyte can be determined from indirect labelling. This is advantageous particularly with respect to the use of mass spectrometry because complex biomolecules such as DNA have complex mass spectra and are detected with relatively poor sensitivity. Indirect detection means that an associated label molecule can be used to identify the original analyte, where the label is designed for sensitive detection and a simple mass spectrum. Simple mass spectra mean that multiple labels can be used to analyse multiple analytes simultaneously.

WO98/31830 describes arrays of nucleic acid probes covalently attached to cleavable labels that are detectable by mass spectrometry which identify the sequence of the covalently linked nucleic acid probe. The labelled probes of this application have the structure Nu-L-M where Nu is a nucleic acid covalently linked to L, a cleavable linker, covalently linked to M, a mass label. Preferred cleavable linkers in this application cleave within the ion source of the mass spectrometer. Preferred mass labels are substituted polyaryl ethers. This application discloses a variety of ionisation methods and analysis by quadrupole mass analysers, TOF analysers and magnetic sector instruments as specific methods of analysing mass labels by mass spectrometry.

WO95/04160 discloses ligands, and specifically nucleic acids, cleavably linked to mass tag molecules. Preferred cleavable linkers are photo-cleavable. This application discloses Matrix Assisted Laser Desorption Ionisation (MALDI) Time of Flight (TOF) mass spectrometry as a specific method of analysing mass labels by mass spectrometry.

WO98/26095 discloses releasable non-volatile mass-label molecules. In preferred embodiments these labels comprise polymers, typically biopolymers which are cleavably attached to a reactive group or ligand, i.e. a probe. Preferred cleavable linkers appear to be chemically or enzymatically cleavable. This application discloses MALDI TOF mass spectrometry as a specific method of analysing mass labels by mass spectrometry.

WO97/27327, WO97/27325, and WO97/27331 disclose ligands, and specifically nucleic acids, cleavably linked to mass tag molecules. Preferred cleavable linkers appear to be chemically or photo-cleavable. These application discloses a variety of ionisation methods and analysis by quadrupole mass analysers, TOF analysers and magnetic sector instruments as specific methods of analysing mass labels by mass spectrometry.

Gygi et al. (Nature Biotechnology 17: 994-999, "Quantitative analysis of complex protein mixtures using isotope-coded affinity tags" 1999) disclose the use of 'isotope encoded affinity tags' for the capture of peptides from proteins, to allow protein expression analysis. In this article, the authors describe the use of a biotin linker, which is reactive to thiols, for the capture of peptides with cysteine in them. A sample of protein from one source is reacted with the biotin linker and cleaved with an endopeptidase. The biotinylated cysteine-containing peptides can then be isolated on avidinated beads for subsequent analysis by mass spectrometry. Two samples can be compared quantitatively by labelling one sample with the biotin linker and labelling the second sample with a deuterated form of the biotin linker. Each peptide in the samples is then represented as a pair of peaks in the mass spectrum. Integration of the peaks in the mass spectrum corresponding to each tag indicate the relative expression levels of the peptide linked to the tags.

This 'isotope encoding' method has a number of limitations. A first is the reliance on the presence of thiols in a protein—many proteins do not have thiols while others have several. In a variation on this method, linkers may be designed to react with other side chains, such as amines. However, since many proteins contain more than one lysine residue, multiple peptides per protein would generally be isolated in this approach. It is likely that this would not reduce the complexity of the sample sufficiently for analysis by mass spectrometry. A sample that contains too many species is likely to suffer from 'ion suppression', in which certain species ionise preferentially over other species which would normally appear in the mass spectrum in a less complex sample.

The second limitation of this approach is the method used to compare the expression levels of proteins from different samples. Labelling each sample with a different isotope variant of the affinity tag results in an additional peak in the mass spectrum for each peptide in each sample. This means that if two samples are analysed together there will be twice as many peaks in the spectrum. Similarly, if three samples are analysed together, the spectrum will be three times more complex than for one sample alone. It is clear that this approach will be limited, since the ever increasing numbers of peaks will increase the likelihood that two different peptides will have overlapping peaks in the mass spectrum.

A further limitation, which is reported by the authors of the above paper, is the mobility change caused by the tags. The authors report that peptides labelled with the deuterated biotin tag elute slightly after the same peptide labelled with the undeuterated tag.

The mass spectra generated for analyte material are very sensitive to contaminants. Essentially, any material introduced into the mass spectrometer that can ionise will appear in the mass spectrum. This means that for many analyses it is necessary to carefully purify the analyte before introducing it into the mass spectrometer. For the purposes of high throughput systems for indirect analysis of analytes through mass labels it would be desirable to avoid any unnecessary sample preparation steps. That is to say it would be desirable to be able to detect labels in a background of contaminating material and be certain that the peak that is detected does in fact correspond to a label. The prior art does not disclose methods or compositions that can improve the signal to noise ratio achievable in mass spectrometry based detection systems or that can provide confirmation that a mass peak in a spectrum was caused by the presence of a mass label.

For the purposes of detection of analytes after liquid chromatography or electrophoretic separations it is desirable that the labels used, minimally interfere with the separation process. If an array of such labels are used, it is desirable that the effect of each member of the array on its associated analyte is the same as every other label. This conflicts to some extent with the intention of mass marking which is to generate arrays of labels that are resolvable in the mass spectrometer on the basis of their mass. It is disclosed in the prior art above that mass labels should preferably be resolved by 4 Daltons to prevent interference of isotope peaks from one label with those of another label. This means that to generate 250 distinct mass labels would require labels spread over a range of about 1000 Daltons and probably more, since it is not trivial to generate large arrays of labels separated by exactly 4 Daltons. This range of mass will almost certainly result in mass labels that will have a distinct effect on any separation process that precedes detection by mass spectrometry. It also has implications for instrument design, in that as the mass range over which a mass spectrometer can detect ions increases, the cost of the instrument increases.

WO 01/68664 and WO 03/025576 disclose sets of mass labels suitable for labelling analytes for subsequent mass spectrometric analysis. The mass labels comprise a mass marker moiety attached via a cleavable linker to a mass normalisation moiety. Sets of such mass labels may comprise a number of mass labels having the same overall mass, but which are nevertheless distinguishable from each other by mass spectrometry by virtue of their mass marker moieties having different masses. Thus mass labels in such a set comprising a mass marker moiety of a higher mass comprise a mass normalisation moiety of a lower mass, and vice versa.

These mass labels are particularly suited to tandem mass spectrometry methods. In a first step, ionised mass labels of a particular mass/charge ratio are selected. In a second step, the selected mass labels are fragmented by collision induced dissociation and the mass marker moieties are detected.

There is however a need for further sets of mass labels which enable large numbers of analytes to be labelled and distinguished by mass spectrometry. In particular, there is a need for sets of mass labels in which large numbers of unique labels can be produced in a simple manner.

Accordingly, the present invention provides a set of mass labels, each mass label in the set comprising a mass marker moiety attached via a cleavable linker to a mass normalisation moiety, each mass label in the set having a common mass; wherein the set comprises a plurality of groups of mass labels, the mass of the mass marker moiety being the same for mass labels within a group, the mass of the mass marker moiety being different between groups; the mass marker moiety is capable of fragmentation into two or more fragments; and the mass of at least one fragment of the mass marker moiety differs between mass labels within a group.

In a further aspect, the present invention provides an array of mass labels, comprising a plurality of sets of mass labels as defined above, wherein the common mass of the mass labels is different for each set.

The sets of mass labels according to the present invention provide an additional dimension in mass labelling, by using mass marker moieties which can be further fragmented. Thus the sets of mass labels according to the present invention (which comprise mass labels having the same overall mass) comprise groups of mass labels which comprise mass marker moieties having the same mass, but which are nevertheless distinguishable from each other by mass spectrometry. This is in contrast to the sets of mass labels of WO 01/68664 and WO 03/025576, where either the overall mass of the mass labels or the mass of the mass marker moieties must be different for the mass labels to be distinguished.

The mass marker and mass normalisation moieties of the mass labels of the present invention can be differentially labelled, such that mass marker moieties having the same mass are distinguishable from one another by virtue of differing masses of corresponding fragments derived from particular mass marker moieties.

In preferred embodiments, mass marker moieties having the same mass can be made distinguishable from one another by isotopic labelling. One or more isotopic labels is included in the mass labels, the position of the isotopic labels varying between mass labels. Thus in any group of mass labels comprising mass marker moieties having a common mass, the isotopic label or labels may be comprised in a different fragment derived from particular mass marker moieties (and thus from particular mass labels).

The isotopic label may comprise an atom or substituent comprising an isotope which occurs naturally in low abundance, such as $^2H$, $^{13}C$, $^{15}N$ or $^{18}O$. The particular nature of the isotopic label is not particularly limited, provided that it allows a fragment comprising the isotopic label to be distinguished from a corresponding fragment which does not comprise the isotopic label, i.e. which contains predominantly naturally occurring isotopes (e.g. $^1H$, $^{12}C$, $^{14}N$ or $^{16}O$).

The use of isotopic labels according to certain embodiments of the present invention allows groups and sets of mass labels to be produced which are chemically identical (i.e. which comprise the same chemical species, but differ only in terms of the isotopic composition at particular positions). This is a simple and efficient way of achieving a large number of distinguishable mass labels, without requiring complicated differential chemical syntheses for each mass label.

Although the prior art has suggested the use of isotopic substituents as a way of varying the mass of mass labels, embodiments of the present invention combine the use of isotopic labelling with mass labels comprising mass marker moieties and mass normalisation moieties. Compared to the method disclosed in WO 01/68664 and WO 03/025576, the present invention permits an additional dimension of mass labelling. Thus each mass label comprising a mass marker moiety of unique mass can be used to generate a plurality of unique mass labels differing in terms of the mass of fragments of the mass marker moiety.

As discussed above, the mass labels disclosed in WO 01/68664 and WO 03/025576 can be distinguished by tandem mass spectrometry. Individual mass labels according to the present invention comprising mass marker moieties having a common mass can be resolved by an additional mass spectrometry step in which the mass marker moiety is fragmented and the fragments detected. Thus the present method may be considered to involve a "triple" mass spectrometry process. In a first stage, the mass labels are separated from the analytes (e.g. by collision induced dissociation in the mass spectrometer) and the mass labels are selected for analysis in the second stage. The mass labels are dissociated in the mass spectrometer in the second stage to release the mass marker moieties from the mass normalisation moieties, the mass marker moieties being selected for further fragmentation and analysis in the third stage.

The additional labelling dimension provided by the present invention can be used practically to resolve experimental information which might previously have been overlooked in order to avoid undesirable complexity. For instance, samples derived from a plurality of experimental conditions may each be labelled with a mass label comprising a different mass marker moiety, so that the amount of an analyte in each sample can be quantified. Typically, each experimental condition may be repeated a number of times in order to establish reproducibility and statistical significance. In a complex experimental protocol involving a large number of different experimental conditions, repeats of each experimental condition may be pooled before labelling (e.g. if only a limited number of mass labels is available or simply to reduce complexity).

However according to the present invention, samples derived from each experimental condition can be labelled with mass labels comprising mass marker moieties having a particular mass, and variation between individual repeats can be detected by labelling samples derived from each repeat with mass labels in which the position of an isotopic label in the mass marker moiety varies. Thus samples derived from repeats of a particular experimental condition are each labelled with a particular mass label from a group of individual mass labels, each mass label in the group having a mass marker moiety of common mass but differing in terms of the masses of fragments of the mass marker moiety. If samples are labelled in this way, performing a two-stage tandem mass spectrometry analysis will give pooled results for each experimental condition. If results for individual repeats for each condition are required, a further mass spectrometry step is performed in which the mass marker moieties are fragmented and the fragments thereof analysed.

The sets of mass labels of the present invention can be detected and identified in a background of contamination. Furthermore the sets and arrays of labels disclosed herein can be resolved in a compressed mass range so that the labels do not substantially interfere with separation processes and they can be detected easily in a mass spectrometer that detects ions over a limited range of mass to charge ratios. The sets of labels of the present invention maximise throughput, signal to noise ratios and sensitivity of assays for biomolecules, particularly for the analysis of peptides.

The term mass marker moiety used in the present context is intended to refer to a moiety that is to be detected by mass spectrometry, whilst the term mass normalisation moiety used in the present context is intended to refer to a moiety that is not necessarily to be detected by mass spectrometry, but is present to ensure that a mass label has a desired aggregate mass.

The number of mass labels in the set is not especially limited, provided that the set comprises a plurality of mass labels. However, it is preferred if the set comprises two or more, three or more, four or more, or five or more mass labels.

The present invention also provides an array of mass labels, comprising two or more sets of mass labels as defined above, wherein the common mass of each of the mass labels in any one set is different from the common mass of each of the mass labels in every other set in the array.

In preferred embodiments of the invention, the mass labels in a group, set or array are all chemically identical. In order to vary the characteristics of the mass labels between groups, the masses of the mass normalisation and mass marker moieties are preferably altered by isotope substitutions. As discussed above, isotope substitutions can also be used to vary the masses of particular fragments of the mass marker moiety within a group.

In further preferred embodiments of this invention, the tags may comprise a sensitivity enhancing group. The tags are preferably of the form:

sensitivity enhancing group-amide bond-linker-reactive functionality

In this example the sensitivity enhancing group is usually attached to the mass marker moiety, since it is intended to increase the sensitivity of the detection of this moiety in the mass spectrometer. The reactive functionality is shown as being present and attached to a different moiety than the sensitivity enhancing group. The sensitivity enhancing group may comprise two components, a first component which enhances MS/MS ion intensity (typically a basic residue) and a second component which enhances MS ion intensity. However, the tags need not be limited in this way and in some cases comprise the sensitivity enhancing group without the reactive functionality. In other embodiments the sensitivity enhancing group may be attached to the same moiety as the reactive functionality.

In certain embodiments of the invention the mass tags comprise an affinity capture reagent. Preferably, the affinity capture ligand is biotin. The affinity capture ligand allows labelled analytes to be separated from unlabelled analytes by capturing them, e.g. on an avidinated solid phase.

In a further aspect the invention provides a method of analysing a biomolecule or a mixture of biomolecules. This method preferably comprises the steps of:
1. Reacting the biomolecule or mixture of biomolecules with a mass label according to this invention;
2. Optionally separating the labelled biomolecule electrophoretically or chromatographically;
3. Ionising the labelled biomolecule;
4. Selecting ions of a predetermined mass to charge ratio corresponding to the mass to charge ratio of the preferred ions of the labelled biomolecule in a mass analyser;
5. Inducing dissociation of these selected ions by collision;
6. Selecting collision product ions comprising the mass marker moieties;
7. Inducing dissociation of the collision product ions comprising the mass marker moieties;
8. Detecting fragments derived from the mass marker moieties.

In this embodiment, where the mass tags comprise an affinity tag, the affinity tagged biomolecules may be captured by a counter-ligand to allow labelled biomolecules to be separated from unlabelled biomolecules. This step preferably takes place prior to the optional second step above.

In certain embodiments the step of selecting the ions of a predetermined mass to charge ratio is performed in the first mass analyser of a serial instrument. The selected ions are then channelled into a separate collision cell where they are collided with a gas or a solid surface according to the fifth step of the first aspect of the invention. The collision products are then channelled into a further mass analyser of a serial instrument to detect collision products according to the sixth step of the first aspect of this invention. Ions corresponding to the mass marker moieties are selected and channelled into a further collision cell where they are dissociated in the seventh step. The fragments of the mass marker moieties are detected in a further mass analyser in the eighth step.

Typical serial instruments include triple quadrupole mass spectrometers, tandem sector instruments and quadrupole time of flight mass spectrometers.

In other embodiments, the step of selecting the ions of a predetermined mass to charge ratio, the step of colliding the selected ions with a gas and the step of detecting the collision products are performed in the same zone of the mass spectrometer. This may effected in ion trap mass analysers and Fourier Transform Ion Cyclotron Resonance mass spectrometers, for example.

In another aspect, this invention provides sets or arrays of mass labelled molecules of the form:

analyte-linker-label where label is a mass marker from a set or array according to this invention, the linker is a linker as described below and analyte may be any analyte of interest such as a biomolecule. One preferred aspect of this embodiment is where the analytes (one, more than one or even all the analytes) in the set or array are standard analytes with a known mass or with predetermined chromatographic properties. Such standards can be employed in the methods of the present invention for comparison with unknown analytes, for example when analysing the results of a chromatographic separation step.

This invention describes mass markers that may be readily produced in a peptide synthesiser. Indeed, the compounds used in this invention comprise peptides and modified peptides. Peptide synthesis provides chemical diversity allowing for a wide range of markers with chosen properties to be produced in an automated fashion.

The term 'MS/MS' in the context of mass spectrometers refers to mass spectrometers capable of selecting ions, subjecting selected ions to Collision Induced Dissociation (CID) and subjecting the fragment ions to further analysis.

The term 'serial instrument' refers to mass spectrometers capable of MS/MS in which mass analysers are organised in series and each step of the MS/MS process is performed one after the other in linked mass analysers. The present invention particularly relates to an 'MS/MS/MS', 'MS$^3$' or 'triple' mass spectrometry method involving three serial analysis steps. Typical serial instruments include triple quadrupole mass spectrometers, tandem sector instruments and quadrupole time of flight mass spectrometers. These instruments may be modified where necessary in order to enable MS$^3$.

The invention will now be described in further detail by way of example only, with reference to the accompanying drawings, in which.

Figure 1:
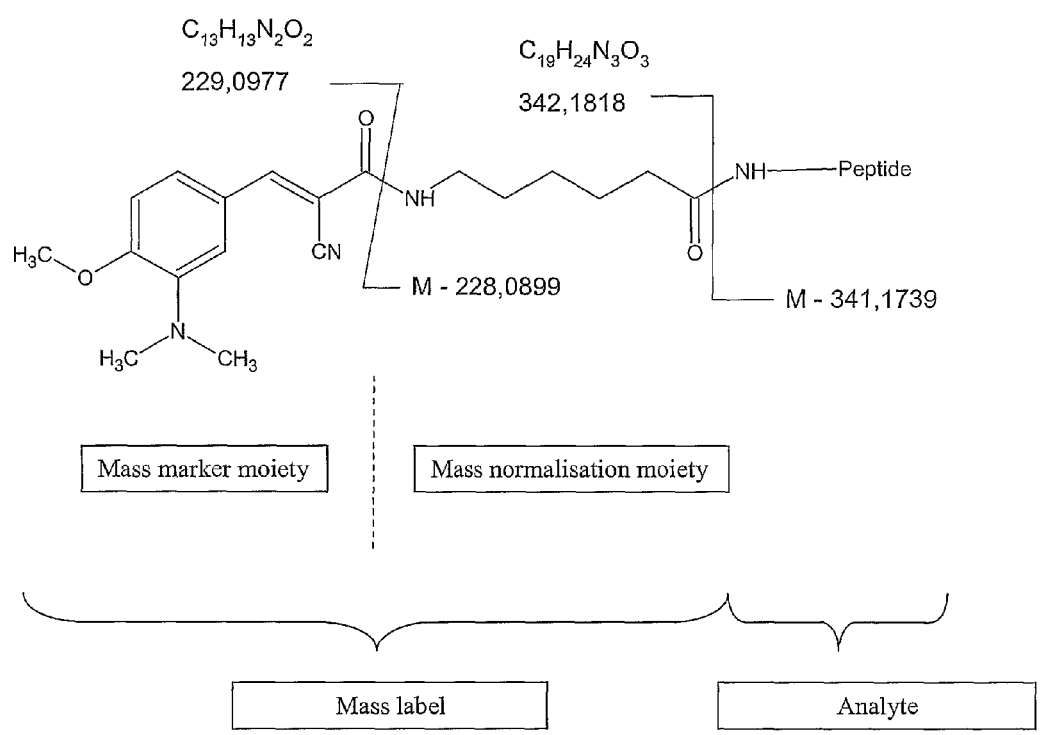
FIG. 1 shows a labelled analyte suitable for use in the present invention.

FIG. 1 shows a labelled analyte suitable for use in the present invention. A peptide (analyte) is attached to a mass label, which comprises a mass marker moiety and a mass normalisation moiety. The mass/charge ratios of ions of the mass label and the mass marker moiety fragments are shown in FIG. 1.

Figure 2:
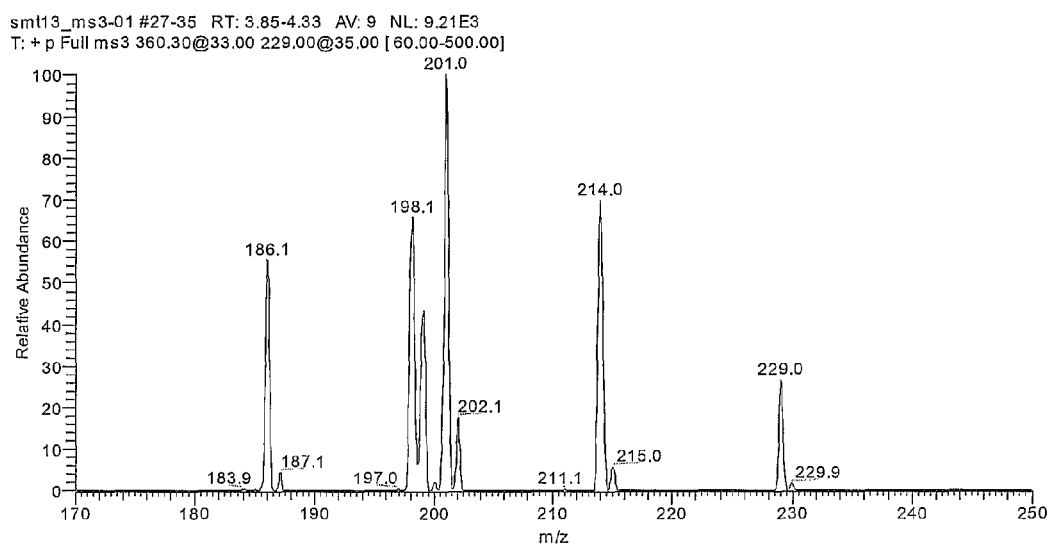
FIG. 2 shows a mass spectrum produced by collision induced dissociation of the mass marker moiety shown in FIG. 1.

FIG. 2 shows a mass spectrum obtained by analysing water as a model analyte labelled with the mass label of FIG. 1 by triple mass spectrometry. In a first step, ions comprising the mass label are selected in a mass spectrometer. These ions are subjected to collision induced dissociation in order to release the mass marker moiety from the mass normalisation moiety. Ions comprising the mass marker moiety are then selected and subjected to a further collision induced dissociation step. The mass spectrum shown represents fragments derived from the mass marker moiety.

Figure 3:
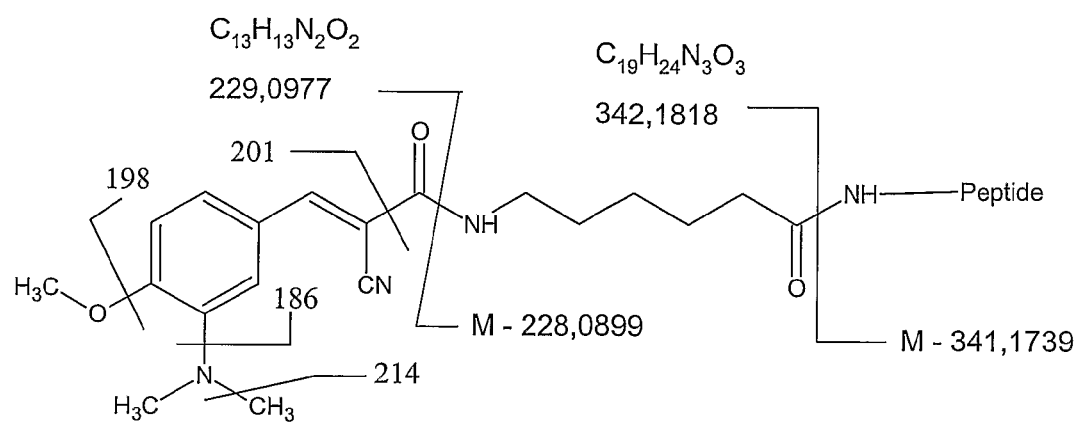
FIG. 3 shows an interpretation of the mass spectrum shown in FIG. 2.

FIG. 3 relates the peaks shown in the mass spectrum of FIG. 2 to the structure of the mass label shown in FIG. 1. The main fragments correspond to major peaks at 186, 198, 201 and 214.

Figure 4:
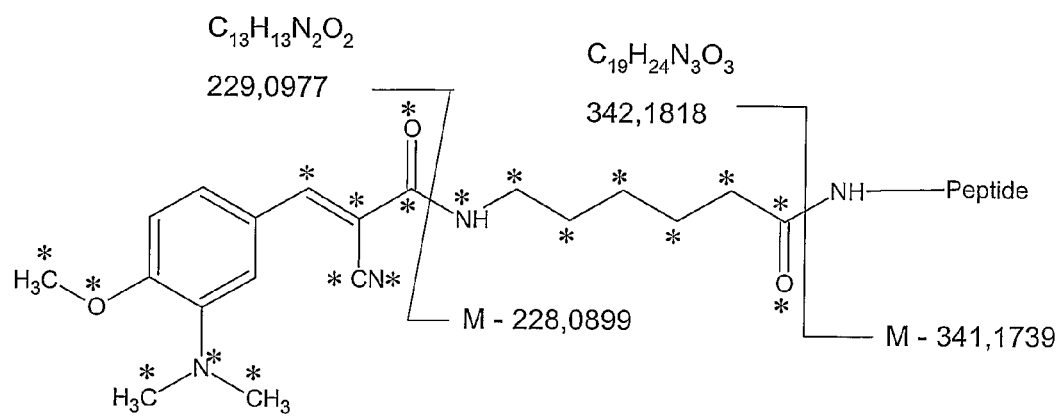
FIG. 4 shows suitable positions for isotopic labelling of the mass label shown in FIG. 1.

FIG. 4 illustrates how the mass label shown in FIG. 1 may be isotopically labelled to produce a set of mass labels comprising an isotopic label at different positions. The mass label may comprise one or more isotopic labels at one or more of the preferred positions marked by an asterisk. Isotopic labels in the mass marker moiety may be placed at different positions such that they appear in different fragments as indicated in FIG. 3, allowing mass marker moieties having the same mass to be distinguished when the mass marker moiety is fragmented. Thus isotopic labels are placed, for example, in substituent groups such as the methoxy or dimethylamino groups rather than in the benzene ring which is resistant to fragmentation. At each position marked by an asterisk, $^1$H, $^{12}$C, $^{14}$N and $^{16}$O may be substituted with $^2$H, $^{13}$C, $^{15}$N and $^{18}$O respectively.

The total number of isotopic labels in the mass marker moiety is varied between groups of mass labels, each group of mass labels comprising mass marker moieties of the same mass. Adding isotopic labels to the mass normalisation moiety can be used to balance the total mass of the mass label between different groups of mass labels, such that the total mass of each mass label in a set is the same despite the number of isotopic labels in the mass marker moiety varying between groups.

Figure 5:
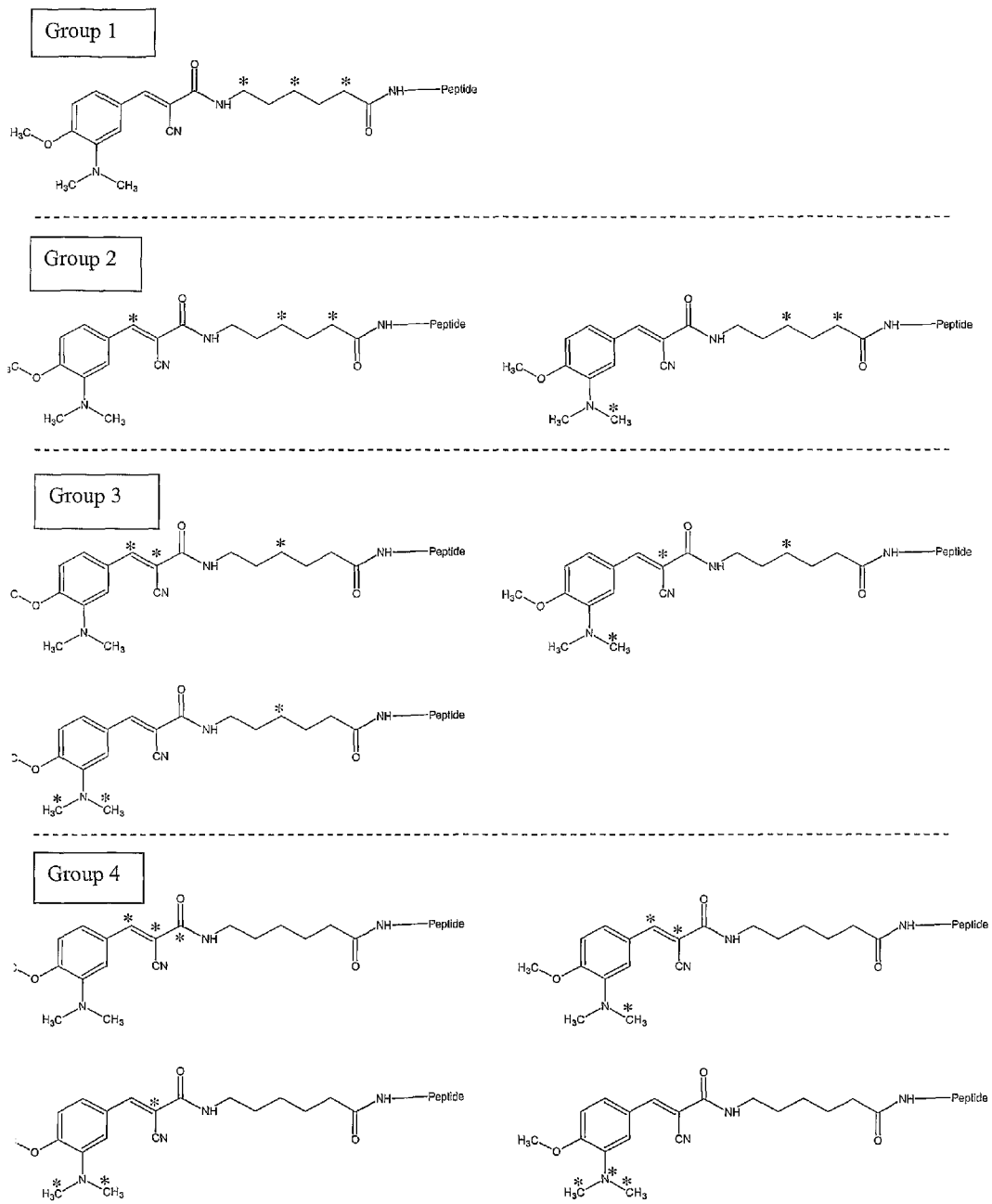
FIG. 5 shows a set of mass labels according to the present invention.
Figure 6A:
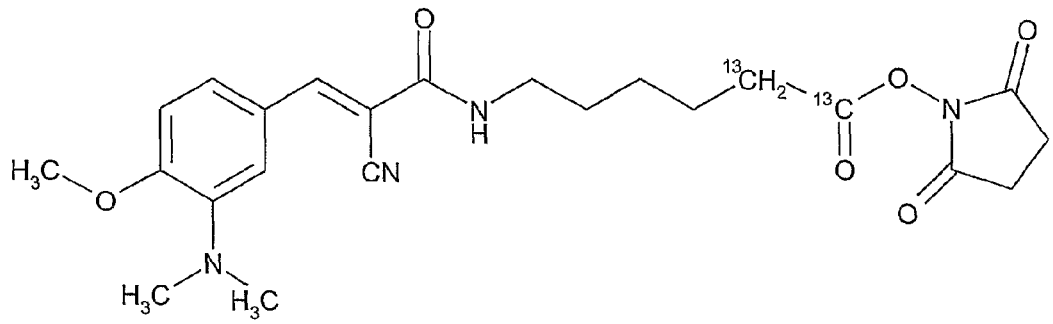
FIG. 6 shows a further set of mass labels labelled at different positions with $^{13}$C.
Figure 6B:
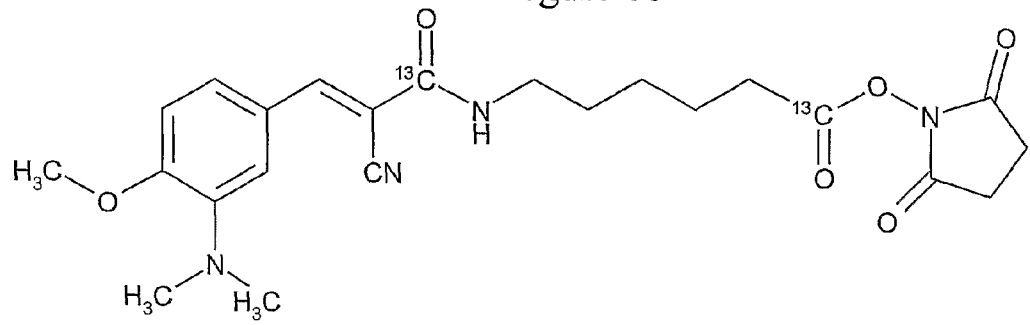
Figure 6C:
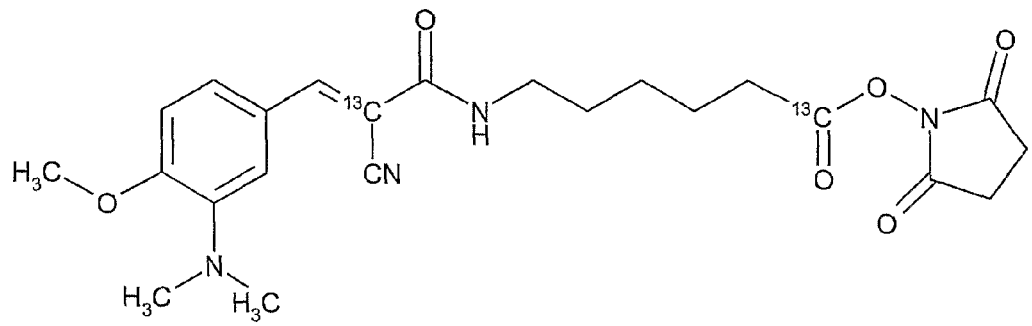
Figure 6D:
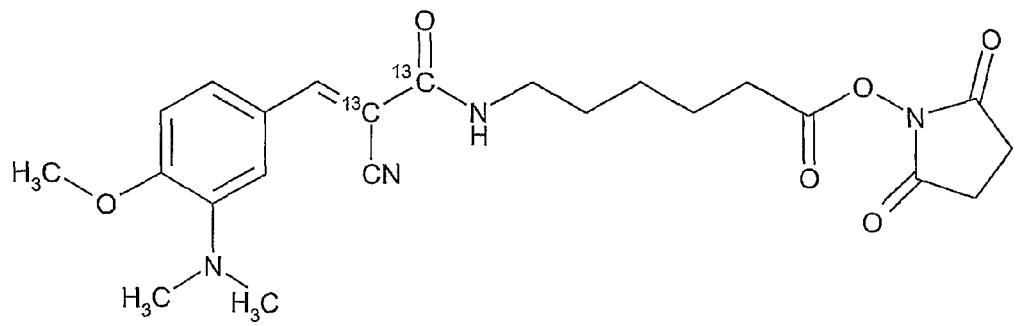

FIG. 5 illustrates how this may be implemented in one set of mass labels according to the present invention. The mass labels are shown attached to analytes as in FIG. 1. Each mass label in the set has a common mass, and its structure is chemically identical to that shown in FIG. 1. Each mass label comprises three isotopic labels, marked by asterisks. The isotopic labels each comprise a $^{13}$C (in place of a $^{12}$C) atom, apart from in one mass label in group 4 which comprises a $^{15}$N atom (in place of a $^{14}$N atom).

The number of isotopic labels in the mass marker moiety (and thus also in the mass normalisation moiety) varies between the groups of mass labels shown in FIG. 5. Thus a mass label in group 1 comprises 3 isotopic labels in the mass normalisation moiety and none in the mass marker moiety. Mass labels in group 2 each comprise 2 isotopic labels in the mass normalisation moiety and 1 in the mass marker moiety. Mass labels in group 3 each comprise 1 isotopic label in the mass normalisation moiety and 2 in the mass marker moiety. Mass labels in group 4 each comprise no isotopic labels in the mass normalisation moiety and 3 in the mass marker moiety. The mass/charge ratio of the mass marker moiety therefore also varies between groups.

FIG. 3 shows that a fragment of the mass marker moiety lacking the dimethylamino group has a mass/charge ratio of 186 (without any isotopic substitution). In the set of mass labels shown in FIG. 5, mass labels within a particular group can be distinguished by the number of isotopic labels present in this fragment. Thus in group 2, the number of isotopic labels in this fragment is either 1 or 0, and the two mass labels in the group are distinguishable by virtue of the mass/charge ratio of this fragment (either 187 or 186). In group 3, the number of isotopic labels in the fragment is either 2, 1 or 0, giving mass/charge ratios of 188, 187 or 186 respectively for fragments derived from different labels. In group 4, the number of isotopic labels in the fragment is either 3, 2, 1 or 0, giving mass/charge ratios of 189, 188, 187 or 186 respectively for corresponding fragments derived from different labels.

The structure of the mass labels shown in FIG. 5 is summarised in the following table:

| Mass label | Isotopic labels in mass marker moiety | Isotopic labels in mass norm. moiety | Isotopic labels in fragment | m/z of mass marker moiety | m/z of fragment |
|---|---|---|---|---|---|
| 1 | 0 | 3 | 0 | 229 | 186 |
| 2a | 1 | 2 | 1 | 230 | 187 |
| 2b | 1 | 2 | 0 | 230 | 186 |
| 3a | 2 | 1 | 2 | 231 | 188 |
| 3b | 2 | 1 | 1 | 231 | 187 |
| 3c | 2 | 1 | 0 | 231 | 186 |
| 4a | 3 | 0 | 3 | 232 | 189 |
| 4b | 3 | 0 | 2 | 232 | 188 |
| 4c | 3 | 0 | 1 | 232 | 187 |
| 4d | 3 | 0 | 0 | 232 | 186 |

Thus each of the mass labels shown in FIG. 5 is distinguishable based on a combination of the m/z ratio of the mass marker moiety and the m/z ratio of the fragment.

The general structures of the mass labels used in the present invention may be based on those described, for example, in WO 01/68664, WO 03/025576, WO 02/099435, WO 03/087839 and WO 2005/012914, provided that the mass labels comprise a mass marker moiety and a mass normalisation moiety. However, the sets of mass labels described herein differ from those described in the above publications because according to the present invention, a set of mass labels contains mass labels comprising mass marker moieties of the same mass, such mass labels nevertheless being distinguishable from one another when the mass marker moieties are fragmented in a mass spectrometer. Thus mass labels for use in the present invention can be produced by taking a particular mass label disclosed in one of the above publications and differentially labelling (e.g. by isotopic labelling) the mass marker moiety to produce a group of mass labels distinguishable only by fragmentation of the mass marker moiety.

In one preferred embodiment, sets of mass labels comprise mass labels based on the structure of sensitizer mass tags as disclosed in WO 2005/012914, but comprising the novel features of the sets of the present invention. In this embodiment, sets of such mass labels are preferably analysed using matrix assisted laser desorption ionisation (MALDI) mass spectrometry.

For example, a mass label which forms the basis for a set of mass labels as shown in FIG. 5 may be synthesised according to the protocol described below. The synthesis is described for a label comprising a terminal 2,5-dioxo-1-pyrrolidinyl ester, rather than a label linked to a peptide as shown in FIG. 5. In the first step a chlorinated linker is produced. The chlorine group is then nucleophilically substituted by a cyanide ion. This cyano linker is then condensed with 3-dimethylamino 4-hydroxybenzaldehyde to give a cinnamic acid derivative with a six carbon chain linker with a free carboxyl group that is activated to form an NHS-ester in the final step of the synthesis.

Synthesis of 6-[2-Cyan-3-(3-dimethylamino-4-methoxy-phenyl)acryloylamino]hexanoic acid-[(2,5-dioxo-1-pyrrolidinyl)ester 1. Synthesis of 6-(chloracetamido)hexanoic acid 18 mL (221 mMol) chloracetylchloride was added dropwise to 20 g (153 mMol) 6-aminohexanoic acid dissolved in 80 mL cold NaOH solution (2 N) at RT. The reaction mixture was stirred for 30 minutes while the pH of the solution was kept between 10 and 11 with occasional addition of NaOH solution (6 N). The pH of the reaction mixture was then altered to pH 5 with HCl (2 N) and the residue was filtered. The residue was then washed with water until the pH of the water was neutral. The product, dried over phosphorus pentoxide, was re-dissolved in 300 ml chloroform and filtered to remove the undissolved residue. Heptane was added to the filtrate and a syrup was obtained by stirring under cooling. The product was filtered, dried and was then crystallized from water.
Yield: 20 g=63%
Melting Point: 82° C.

2. Synthesis of 6-(cyanacetamido)hexanoic acid 2.8 g (20 mMol) potassium hydrogen carbonate was added to 8.3 g (40 mMol) 6-(chloracetamido) hexanoic acid dissolved in 25 ml water. 3.2 g (48 mMol) potassium cyanide was then added to the clear solution which was cooled on ice. The reaction mixture was stirred for 17 hours and was then acidified with HCl (2 N). The residue after extraction was purified by chromatography (silica gel, solvent: ethyl acetate).
Yield: 6 g=76%
Melting Point: 80-81° C.

3. Synthesis of 6-[2-cyan-3-(3-dimethylamino-4-methoxy-phenyl)acryloylamino]hexanoic acid 3.96 g (20 mMol 6-(2-cyan-acetylamino)hexanoic acid was dissolved in 27 ml pyridine. 3.64 g (20 mMol) 3-dimethylamino-4-methoxybenzaldehyde and 0.6 mL piperidine were added to the solution and the reaction mixture was stirred for 20 hours. After evaporation of the reaction mixture the residue was solved in 150 ml ethyl acetate and 150 ml water and the pH was adjusted with pure acetic acid to 4.2. The aqueous phase was extracted with ethyl acetate. The collected ethyl acetate phases were washed with NaCl-Solution, dried and evaporated. The residue was chromatographed on $SiO_2$ with ethyl acetate under low pressure. The product was crystallized from little ethyl acetate.
Yield: 4.6 g=66%
Melting Point: 130° C.

4. Synthesis of 6-[2-cyan-3-(3-dimethylamino-4-methoxy-phenyl)acryloylamino]hexanoic acid-[(2,5-dioxo-1-pyrrolidinyl)ester 0.78 g (6.76 Mol) N-hydroxysuccinimide and 2.43 g (6.76 mMol) 6-[2-Cyan-3-(3-dimethylamino-4-methoxy-phenyl)acryloylamino]hexanoic acid were added to 50 ml $CH_2Cl_2$. The mixture was stirred at room temperature for 20 h. The solution was filtered and evaporated. The residue was chromatographed on Florisil with ethyl acetate under low pressure. The crystalline product was pasted with diisopropylether and collected on a filter.
Yield: 1.9 g=62%
Melting Point: 104° C.

The above protocol can be varied in order to allow incorporation of isotopic labels into different positions in the mass label. Appropriately $^{13}$C-labelled starting materials can be used in order to give a $^{13}$C label at a predetermined position in the final product. For instance, one or both carbon atoms in the chloracetylchloride (or alternatively bromoacetylchloride) which is used in step 1 above can be $^{13}$C labelled. The $^{13}$C-labelled chloracetylchloride or bromoacetylchloride may be obtained, for instance, from $^{13}$C-labelled chloro- or bromoacetic acid (hereinafter Reagent A).

In a similar way, the 6-aminohexanoic acid used in step 1 may be labelled at various positions with a $^{13}$C atom. $^{13}$C-labelled 6-aminohexanoic acid may be obtained, for instance, by reacting $^{13}$C-labelled acetic acid (hereinafter Reagent B) with Boc-4-aminobutylbromide under alkaline conditions (lithium diisopropylamide) to form $^{13}$C-labelled Boc-6-aminohexanoic acid, and removing the t-butyloxycarbonyl (Boc) protecting group under HCl treatment.

FIG. 6 shows 4 mass labels based on the molecule the synthesis of which is described above. Each of the mass labels 6a-d has the same overall mass. Each mass label comprises two $^{13}$C isotopic labels. The mass labels 6a-d can be synthesised using the following starting materials to prepare the reagents used in step 1 of the protocol given above:

| Mass label | m/z of mass marker moiety | m/z of fragment A | m/z of fragment B | Starting materials | |
|---|---|---|---|---|---|
| | | | | Reagent A | Reagent B |
| 6a | 229 | 198 | 201 | BrCH$_2$COOH | $^{13}$CH$_3$$^{13}$COOH |
| 6b | 230 | 199 | 201 | BrCH$_2$$^{13}$COOH | CH$_3$$^{13}$COOH |
| 6c | 230 | 199 | 202 | Br$^{13}$CH$_2$COOH | CH$_3$$^{13}$COOH |
| 6d | 231 | 200 | 202 | Br$^{13}$CH$_2$$^{13}$COOH | CH$_3$COOH |

Fragment A is a fragment of the mass marker moiety having a m/z of 198 in the non-isotopically labelled mass label shown in FIG. 3. Fragment B is a fragment of the mass marker moiety having a m/z of 201 in the non-isotopically labelled mass label shown in FIG. 3.

The set of mass labels need not be limited to the preferred embodiments described above, and may for example comprise labels of multiple types, provided that all labels are distinguishable by mass spectrometry, as outlined above.

It is preferred that each mass marker moiety in the set has a common basic structure and each mass normalisation moiety in the set has a common basic structure, and each mass label in the set comprises one or more mass adjuster moieties, the mass adjuster moieties being attached to or situated within the basic structure of the mass marker moiety and/or the basic structure of the mass normalisation moiety. In this embodiment, the number of mass adjuster moieties in the mass marker moiety differs between groups of labels and each mass label in the set comprises the same total number of mass adjuster moieties.

By common basic structure, it is meant that two or more moieties share a structure which has substantially the same structural skeleton, backbone or core. This skeleton or backbone may be for example comprise one or more amino acids. Preferably the skeleton comprises a number of amino acids linked by amide bonds. However, other units such as aryl ether units may also be present. The skeleton or backbone may comprise substituents pendent from it, or atomic or isotopic replacements within it, without changing the common basic structure.

The present invention also encompasses arrays of a plurality of sets of mass labels. The arrays of mass labels of the present invention are not particularly limited, provided that they contain a plurality of sets of mass labels according to the present invention. It is preferred that the arrays comprise two or more, three or more, four or more, or five or more sets of mass labels.

Linker Groups

In the discussion above and below reference is made to linker groups which may be used to collect molecules of interest to the mass label compounds of this invention. A variety of linkers is known in the art which may be introduced between the mass labels of this invention and their covalently attached analyte. Some of these linkers may be cleavable. Oligo- or poly-ethylene glycols or their derivatives may be used as linkers, such as those disclosed in Maskos, U. & Southern, E. M. Nucleic Acids Research 20: 1679-1684, 1992. Succinic acid based linkers are also widely used, although these are less preferred for applications involving the labelling of oligonucleotides as they are generally base labile and are thus incompatible with the base mediated de-protection steps used in a number of oligonucleotide synthesisers.

Propargylic alcohol is a bifunctional linker that provides a linkage that is stable under the conditions of oligonucleotide synthesis and is a preferred linker for use with this invention in relation to oligonucleotide applications. Similarly 6-aminohexanol is a useful bifunctional reagent to link appropriately functionalised molecules and is also a preferred linker.

A variety of known cleavable linker groups may be used in conjunction with the compounds of this invention, such as photocleavable linkers. Ortho-nitrobenzyl groups are known as photocleavable linkers, particularly 2-nitrobenzyl esters and 2-nitrobenzylamines, which cleave at the benzylamine bond. For a review on cleavable linkers see Lloyd-Williams et al., Tetrahedron 49, 11065-11133, 1993, which covers a variety of photocleavable and chemically cleavable linkers.

WO 00/02895 discloses the vinyl sulphone compounds as cleavable linkers, which are also applicable for use with this invention, particularly in applications involving the labelling of polypeptides, peptides and amino acids. The content of this application is incorporated by reference.

WO 00/02895 discloses the use of silicon compounds as linkers that are cleavable by base in the gas phase. These linkers are also applicable for use with this invention, particularly in applications involving the labelling of oligonucleotides. The content of this application is incorporated by reference.

The mass labels of the present invention may comprise reactive functionalities, Re, to help attach them to analytes. In preferred embodiments of the present invention, Re is a reactive functionality or group which allows the mass label to be reacted covalently to an appropriate functional group in an analyte molecule, such as, but not limited to, a nucleotide oligonucleotide, polynucleotide, amino acid, peptide or polypeptide. Re may be attached to the mass labels via a linker which may or may not be cleavable. A variety of reactive functionalities may be introduced into the mass labels of this invention.

Table 1 below lists some reactive functionalities that may be reacted with nucleophilic functionalities which are found in biomolecules to generate a covalent linkage between the two entities. For applications involving synthetic oligonucleotides, primary amines or thiols are often introduced at the 5 termini of the molecules to permit labelling. Any of the functionalities listed below could be introduced into the compounds of this invention to permit the mass markers to be attached to a molecule of interest. A reactive functionality can be used to introduce a further linker groups with a further reactive functionality if that is desired. Table 1 is not intended to be exhaustive and the present invention is not limited to the use of only the listed functionalities.

TABLE 1

| Nucleophilic Functionality | Reactive Functionality | Resultant Linking Group |
|---|---|---|
| —SH | —SO$_2$—CH=CR$_2$ | —S—CR$_2$—CH$_2$—SO$_2$— |
| —NH$_2$ | —SO$_2$—CH=CR$_2$ | —N(CR$_2$—CH$_2$—SO$_2$—)$_2$ or —NH—CR$_2$—CH$_2$—SO$_2$— |
| —NH$_2$ | N-hydroxysuccinimide ester | —CO—NH— |
| —NH$_2$ | hydroxybenzotriazole ester | —CO—NH— |
| —NH$_2$ | —NCO | —NH—CO—NH— |
| —NH$_2$ | —NCS | —NH—CS—NH— |
| —NH$_2$ | —CHO | —CH$_2$—NH— |
| —NH$_2$ | —SO$_2$Cl | —SO$_2$—NH— |
| —NH$_2$ | —CH=CH— | —NH—CH$_2$—CH$_2$— |
| —OH | —OP(NCH(CH$_3$)$_2$)$_2$ | —OP(=O)(O)O— |

It should be noted that in applications involving labelling oligonucleotides with the mass markers of this invention, some of the reactive functionalities above or their resultant linking groups might have to be protected prior to introduction into an oligonucleotide synthesiser. Preferably unprotected ester, thioether and thioesters, amine and amide bonds are to be avoided, as these are not usually stable in an oligonucleotide synthesiser. A wide variety of protective groups is known in the art which can be used to protect linkages from unwanted side reactions.

In the discussion below reference is made to "charge carrying functionalities" and solubilising groups. These groups may be introduced into the mass labels such as in the mass markers of the invention to promote ionisation and solubility. The choice of markers is dependent on whether positive or negative ion detection is to be used. Table 2 below lists some functionalities that may be introduced into mass markers to promote either positive or negative ionisation. The table is not intended as an exhaustive list, and the present invention is not limited to the use of only the listed functionalities.

TABLE 2

| Positive Ion Mode | Negative Ion Mode |
|---|---|
| —NH$_2$ | —SO$_3$— |
| —NR$_2$ | —PO$_4$— |
| —NR$_3^+$ | —PO$_3$— |
| guanidinium group | —CO$_2$— |

TABLE 2-continued

| Positive Ion Mode | Negative Ion Mode |
|---|---|
| N-alkyl pyridinium | |
| —SR$_2^+$ | |

WO 00/02893 discloses the use of metal-ion binding moieties such as crown-ethers or porphyrins for the purpose of improving the ionisation of mass markers. These moieties are also be applicable for use with the mass markers of this invention.

The components of the mass markers of this invention are preferably fragmentation resistant so that the site of fragmentation of the markers can be controlled by the introduction of a linkage that is easily broken by Collision Induced Dissociation (CID). However, it is important that the mass marker moiety is capable of fragmentation into two or more fragments. Aryl ethers are an example of a class of fragmentation resistant compounds that may be used in this invention. These compounds are also chemically inert and thermally stable.

WO 99/32501 discusses the use of poly-ethers in mass spectrometry in greater detail and the content of this application is incorporated by reference.

In the past, the general method for the synthesis of aryl ethers was based on the Ullmann coupling of arylbromides with phenols in the presence of copper powder at about 200° C. (representative reference: H. Stetter, G. Duve, Chemische Berichte 87 (1954) 1699). Milder methods for the synthesis of aryl ethers have been developed using a different metal catalyst but the reaction temperature is still between 100 and 120° C. (M. Iyoda, M. Sakaitani, H. Otsuka, M. Oda, Tetrahedron Letters 26 (1985) 477). This is a preferred route for the production of poly-ether mass labels. See synthesis of FT77 given in the examples below. A recently published method provides a most preferred route for the generation of poly-ether mass labels as it is carried out under much milder conditions than the earlier methods (D. E. Evans, J. L. Katz, T. R. West, Tetrahedron Lett. 39 (1998) 2937).

The present invention also provides a set of two or more probes, each probe in the set being different and being attached to a unique mass label or a unique combination of mass labels, from a set or an array of mass labels as defined as defined above.

Further provided is an array of probes comprising two or more sets of probes, wherein each probe in any one set is attached to a unique mass label, or a unique combination of mass labels, from a set of mass labels as defined above, and wherein the probes in any one set are attached to mass labels from the same set of mass labels, and each set of probes is attached to mass labels from unique sets of mass labels from an array of mass labels as defined above.

In one embodiment, each probe is preferably attached to a unique combination of mass labels, each combination being distinguished by the presence or absence of each mass label in the set of mass labels and/or the quantity of each mass label attached to the probe. This is termed the "mixing mode" of the present invention, since the probes may be attached to a mixture of mass labels.

In the above aspects, the nature of the probe is not particularly limited. However, preferably each probe comprises a biomolecule. Any biomolecule can be employed, but the biomolecule is preferably selected from a DNA, an RNA, an oligonucleotide, a nucleic acid base, a peptide, a polypeptide, a protein and an amino acid.

In one preferred embodiment, this invention provides sets and arrays of mass labelled analytes, such as nucleotides, oligonucleotides and polynucleotides, of the form:

analyte—linker—label

Wherein the linker is a linker as defined above, and label is a mass label from any of the sets and arrays defined above.

In the above aspect, the nature of the analyte is not particularly limited. However, preferably each analyte comprises a biomolecule. Any biomolecule can be employed, but the biomolecule is preferably selected from a DNA, an RNA, an oligonucleotide, a nucleic acid base, a peptide, a polypeptide, a protein and an amino acid.

In one embodiment, each analyte is preferably attached to a unique combination of mass labels, each combination being distinguished by the presence or absence of each mass label in the set of mass labels and/or the quantity of each mass label attached to the probe. As mentioned above, this is termed the "mixing mode" of the present invention, since the probes may be attached to a mixture of mass labels.

As mentioned above, the present invention provides a method of analysis, which method comprises detecting an analyte by identifying by mass spectrometry a mass label or a combination of mass labels unique to the analyte, wherein the mass label is a mass label from a set or an array of mass labels as defined above. The type of method is not particularly limited, provided that the method benefits from the use of the mass labels of the present invention to identify an analyte. The method may be, for example, a method of sequencing nucleic acid or a method of profiling the expression of one or more genes by detecting quantities of protein in a sample. The method is especially advantageous, since it can be used to readily analyse a plurality of analytes simultaneously. However, the method also has advantages for analysing single analytes individually, since using the present mass labels, mass spectra which are cleaner than conventional spectra are produced, making the method accurate and sensitive.

In a further preferred embodiment, the present invention provides a method which method comprises:

(a) contacting one or more analytes with a set of probes, or an array of probes, each probe in the set or array being specific to at least one analyte, wherein the probes are as defined above, (b) identifying an analyte, by detecting the probe specific to that analyte.

In this embodiment it is preferred that the mass label is cleaved from the probe prior to detecting the mass label by mass spectrometry.

The nature of the methods of this particular embodiment is not especially limited. However, it is preferred that the method comprises contacting one or more nucleic acids with a set of hybridisation probes. The set of hybridisation probes typically comprises a set of up to 256 4-mers, each probe in the set having a different combination of nucleic acid bases. This method may be suitable for identifying the presence of target nucleic acids, or alternatively can be used in a stepwise method of primer extension sequencing of one or more nucleic acid templates.

The mass labels of the present invention are particularly suitable for use in methods of 2-dimensional analysis, primarily due to the large number of mass labels that can be simultaneously distinguished. The labels may thus be used in a method of 2-dimensional gel electrophoresis, or in a method of 2-dimensional mass spectrometry.

Mass Modified Amino Acids

A variety of amino acids can be used in the mass marker moiety and the mass normalisation moiety. Neutral amino acids are preferred in the mass normalisation moiety and charged amino acids are preferred in the mass marker moieties (since this facilitates ionisation and increases sensitivity) e.g. in the position marked amino acid 1 and amino acid 2 in the first and fourth embodiments of this invention. A number of commercially available isotopically mass modified amino acids are shown in Table 5 below. Any combination of 1, 2, 3, or 4 or more amino acids from this list are preferred in each of the moieties according to the present invention. It is additionally important according to the present invention that the mass marker moiety itself is differentially modified in different mass labels within a group, such that fragments of the mass marker moiety have differing masses in different mass labels. This can be done, for example, by differential isotopic labelling of a particular combination of amino acids which forms a mass marker moiety in a group of mass labels.

TABLE 5

| Amino acid | Isotope Forms |
|---|---|
| Alanine | $CH_3CH(NH_2)^{13}CO_2H$, $CH_3CD(NH_2)CO_2H$, $CH_3^{13}CH(^{15}NH_2)CO_2H$, $CD_3CH(NH_2)CO_2H$, $CD_3CD(NH_2)CO_2H$, $CD_3CH(NH_3)^{13}CO_2H$, $CD_3^{13}CH(NH_2)CO_2H$, $^{13}CH_3^{13}CH(^{15}NH_2)^{13}CO_2H$ |
| Arginine | $[(^{15}NH_2)_2CNHCH_2CH_2CH(NH_2)CO_2H]^+$ |
| Asparagine | $H_2N^{13}COCH_2CH(NH_2)CO_2H$, $H_2N^{13}CO^{13}CH_2^{13}CH(NH_2)^{13}CO_2H$, $H_2^{15}NCOCH_2CH(NH_2)CO_2H$, $H_2^{15}NCOCH_2CH(^{15}NH_2)CO_2H$ |
| Aspartic Acid | $HO_2^{13}CCH_2CH(NH_2)CO_2H$, $HO_2C^{13}CH_2CH(NH_2)CO_2H$, $HO_2CCH_2CH(NH_2)^{13}CO_2H$, $HO_2^{13}CCH_2CH(NH_2)^{13}CO_2H$, $HO_2CCH_2^{13}CH(NH_2)CO_2H$, $HO_2^{13}C^{13}CH_2CH(NH_2)CO_2H$, $HO_2^{13}C^{13}CH_2^{13}CH(NH_2)^{13}CO_2H$, $HO_2CCD_2CD(NH_2)CO_2H$, $HO_2CCH_2CH(^{15}NH_2)CO_2H$, $HO_2CCH_2CH(^{15}NH_2)^{13}CO_2H$ |
| Cysteine | Not available |
| Glutamic Acid | $HO_2CCH_2CH_2CH(NH_2)^{13}CO_2H$, $HO_2CCH_2CH_2^{13}CH(NH_2)CO_2H$, $HO_2CCH_2^{13}CH_2CH(NH_2)CO_2H$, $HO_2C^{13}CH_2CH_2CH(NH_2)CO_2H$, $HO_2^{13}CCH_2CH_2CH(NH_2)CO_2H$, $HO_2^{13}C^{13}CH_2^{13}CH_2^{13}CH(NH_2)^{13}CO_2H$, $HO_2CCD_2CH_2CH(NH_2)CO_2H$, $HO_2CCD_2CD_2CD(NH_2)CO_2H$, $HO_2^{13}C^{13}CH_2^{13}CH_2^{13}CH(^{15}NH_2)^{13}CO_2H$ |
| Glutamine | $H_2NCOCH_2CH_2CH(NH_2)^{13}CO_2H$, $H_2N^{13}COCH_2CH_2CH(NH_2)CO_2H$, $H_2NCOCD_2CD_2CD(NH_2)CO_2H$, $H_2^{15}NCOCH_2CH_2CH(NH_2)CO_2H$, $H_2NCOCH_2CH_2CH(^{15}NH_2)CO_2H$, $H_2^{15}NCOCH_2CH_2CH(^{15}NH_2)CO_2H$, $H_2^{15}N^{13}CO^{13}CH_2^{13}CH_2^{13}CH(^{15}NH_2)^{13}CO_2H$ |
| Glycine | $H_2NCH_2^{13}CO_2H$, $H_2N^{13}CH_2CO_2H$, $H_2N^{13}CH_2^{13}CO_2H$, $H_2NCD_2CO_2H$, $H_2^{15}NCH_2CO_2H$, $H_2^{15}N^{13}CH_2CO_2H$, $H_2^{15}NCH_2^{13}CO_2H$, $H_2^{15}N^{13}CH_2^{13}CO_2H$ |
| Histidine | $(CH)_2N_2CCH_2CH(NH_2)^{13}CO_2H$, $(CH)_2N_2CCH_2CH(^{15}NH_2)CO_2H$, $(CH)_2^{15}N_2CCH_2CH(NH_2)CO_2H$ |
| Isoleucine | Not available |
| Leucine | $(CH_3)_2CHCH_2CH(NH_2)^{13}CO_2H$, $(CH_3)_2CHCH_2^{13}CH(NH_2)CO_2H$, $(CH_3)_2CHCH_2^{13}CH(NH_2)^{13}CO_2H$, $(CH_3)_2CHCH_2CD(NH_2)CO_2H$, $(CH_3)_2CHCD_2CD(NH_2)CO_2H$, $(CD_3)(CH_3)CHCH_2CH(NH_2)CO_2H$, $(CD_3)_2CDCH_2CH(NH_2)CO_2H$, $(CD_3)_2CDCD_2CD(NH_2)CO_2H$, $(CH_3)_2CHCH_2CH(^{15}NH_2)CO_2H$, $(CH_3)_2CHCH_2CH(^{15}NH_2)^{13}CO_2H$ |
| Lysine | $H_2NCH_2CH_2CH_2CH_2CH(NH_2)^{13}CO_2H$, $H_2NCH_2CH_2CH_2CH_2^{13}CH(NH_2)CO_2H$, $H_2N^{13}CH_2CH_2CH_2CH_2CH(NH_2)CO_2H$, $H_2NCH_2CH_2CH_2CH_2^{13}CH(NH_2)^{13}CO_2H$, $H_2NCH_2CD_2CD_2CH_2CH(NH_2)CO_2H$, $H_2NCD_2CD_2CD_2CD_2CH(NH_2)CO_2H$, $H_2NCH_2CH_2CH_2CH_2CH(^{15}NH_2)CO_2H$, $H_2^{15}NCH_2CH_2CH_2CH_2CH(NH_2)CO_2H$, $H_2^{15}N^{13}CH_2CH_2CH_2CH_2CH(NH_2)CO_2H$ |
| Methionine | $CH_3SCH_2CH_2CH(NH_2)^{13}CO_2H$, $CH_3SCH_2CH_2^{13}CH(NH_2)CO_2H$, $^{13}CH_3SCH_2CH_2CH(NH_2)CO_2H$, $CH_3SCH_2CH_2CD(NH_2)CO_2H$, $CD_3SCH_2CH_2CH(NH_2)CO_2H$, $CH_3SCH_2CH_2CH(^{15}NH_2)CO_2H$, $^{13}CD_3SCH_2CH_2CH(NH_2)CO_2H$, $CH_3SCH_2CH_2^{13}CH(^{15}NH_2)CO_2H$ |
| Phenylalanine | $C_6H_5CH_2CH(NH_2)^{13}CO_2H$, $C_6H_5CH_2^{13}CH(NH_2)CO_2H$, $^{13}C_6H_5CH_2CH(NH_2)CO_2H$, $C_6H_5CH_2CD(NH_2)CO_2H$, $C_6H_5CD_2CH(NH_2)CO_2H$, $C_6D_5CH_2CH(NH_2)CO_2H$, $C_6D_5CD_2CD(NH_2)CO_2H$, $C_6H_5CH_2CH(^{15}NH_2)CO_2H$ |
| Proline | 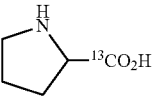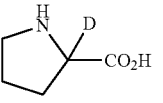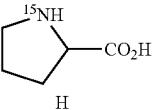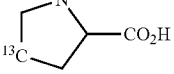 |

TABLE 5-continued

| Amino acid | Isotope Forms |
|---|---|
| Serine | $HOCH_2CH(NH_2)^{13}CO_2H$, $HOCH_2{}^{13}CH(NH_2)CO_2H$, $HO^{13}CH_2CH(NH_2)CO_2H$, $HOCH_2CH(^{15}NH_2)CO_2H$, $HOCH_2{}^{13}CH(^{15}NH_2)CO_2H$ |
| Threonine | $CH_3CH(OH)CH(NH_2)^{13}CO_2H$ |
| Tryptophan | 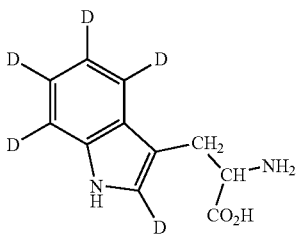 [SMILES: [2H]c1[nH]c2c([2H])c([2H])c([2H])c([2H])c2c1CC(N)C(=O)O] |
| Tyrosine | $HO(C_6H_4)CH_2CH(NH_2)^{13}CO_2H$, $HO(C_6H_4)CH_2{}^{13}CH(NH_2)CO_2H$, $HO(C_6H_4)^{13}CH_2CH(NH_2)CO_2H$, $HO(C_6H_4)^{13}CH_2{}^{13}CH(NH_2)^{13}CO_2H$, $HO(^{13}C_6H_4)CH_2CH(NH_2)CO_2H$, $HO(^{13}C_6H_4)^{13}CH_2{}^{13}CH(NH_2)^{13}CO_2H$, $HO(C_6H_4)CD_2CH(NH_2)CO_2H$, $HO(C_6D_2H_2)CH_2CH(NH_2)CO_2H$, $HO(C_6D_4)CH_2CH(NH_2)CO_2H$, $HO(C_6H_4)CH_2CH(^{15}NH_2)CO_2H$, $H^{17}O(C_6H_4)CH_2CH(NH_2)CO_2H$, $H^{18}O(C_6H_4)CH_2CH(NH_2)CO_2H$, $HO(C_6H_4)CH_2{}^{13}CH(^{15}NH_2)CO_2H$, $HO(^{13}C_6H_4)^{13}CH_2{}^{13}CH(^{15}NH_2)^{13}CO_2H$ |
| Valine | $(CH_3)_2CHCH(NH_2)^{13}CO_2H$, $(CH_3)_2CH^{13}CH(NH_2)CO_2H$, $(CH_3)_2CHCD(NH_2)CO_2H$, $(CD_3)_2CDCD(NH_2)CO_2H$, $(CH_3)_2CHCH(^{15}NH_2)CO_2H$ |

Reactive Functionalities

In some aspects of this invention, as already explained, the mass tags of the invention comprise a reactive functionality. In the simplest embodiments this may be an N-hydroxysuccinimide ester introduced by activation of the C-terminus of the tag peptides of this invention. In conventional synthesis, this activation step would have to take place after the peptide mass tag has been purified from the raw products of its synthesis. An N-hydroxysuccinimide activated mass tag could also be reacted with hydrazine to give a hydrazide reactive functionality, which can be used to label periodate oxidised sugar moieties, for example. Amino-groups or thiols can be used as reactive functionalities in some applications and these may be introduced by adding lysine or cysteine after the linker of the tag. Lysine can be used to couple tags to free carboxyl functionalities using a carbodiimide as a coupling reagent. Lysine can also be used as the starting point for the introduction of other reactive functionalities into the tag of this invention. The thiol-reactive maleimide functionality can be introduced by reaction of the lysine epsilon amino group with maleic anhydride. The cysteine thiol group can be used as the starting point for the synthesis of a variety of alkenyl sulphone compounds, which are useful protein labelling reagents that react with thiols and amines. Compounds such as aminohexanoic acid can be used to provide a spacer between the mass marker moiety and the mass normalisation moiety.

Affinity Capture Ligands

In certain embodiments of the first aspect of this invention the mass markers comprise an affinity capture ligand. Affinity capture ligands are ligands, which have highly specific binding partners. These binding partners allow molecules tagged with the ligand to be selectively captured by the binding partner. Preferably a solid support is derivitised with the binding partner so that affinity ligand tagged molecules can be selectively captured onto the solid phase support. A preferred affinity capture ligand is biotin, which can be introduced into the peptide mass tags of this invention by standard methods known in the art. In particular a lysine residue may be incorporated after amino acid 2 through which an amine-reactive biotin can be linked to the peptide mass tags (see for example Geahlen R. L. et al., Anal Biochem 202(1): 68-67, "A general method for preparation of peptides biotinylated at the carboxy terminus." 1992; Sawutz D. G. et al., Peptides 12(5): 1019-1012, "Synthesis and molecular characterization of a biotinylated analog of [Lys]bradykinin." 1991; Natarajan S. et al., Int J Pept Protein Res 40(6): 567-567, "Site-specific biotinylation. A novel approach and its application to endothelin-1 analogs and PTH-analog.", 1992). Iminobiotin is also applicable. A variety of avidin counter-ligands for biotin are available, which include monomeric and tetrameric avidin and streptavidin, all of which are available on a number of solid supports.

Other affinity capture ligands include digoxigenin, fluorescein, nitrophenyl moieties and a number of peptide epitopes, such as the c-myc epitope, for which selective monoclonal antibodies exist as counter-ligands. Metal ion binding ligands such as hexahistidine, which readily binds $Ni^{2+}$ ions, are also applicable. Chromatographic resins, which present iminodiacetic acid chelated $Ni^{2+}$ ions are commercially available, for example. These immobilised nickel columns may be used to capture peptide mass tags, which comprise oligomeric histidine. As a farther alternative, an affinity capture functionality may be selectively reactive with an appropriately derivitised solid phase support. Boronic acid, for example, is known to selectively react with vicinal cis-diols and chemically similar ligands, such as salicylhydroxamic acid. Reagents comprising boronic acid have been developed for protein capture onto solid supports derivitised with salicylhydroxamic acid (Stolowitz M. L. et al., Bioconjug Chem 12(2): 229-239, "Phenylboronic Acid-Salicylhydroxamic Acid Bioconjugates. 1. A Novel Boronic Acid Complex for Protein Immobilization." 2001; Wiley J. P. et al., Bioconjug Chem 12(2): 240-250, "Phenylboronic Acid-Salicylhydroxamic Acid Bioconjugates. 2. Polyvalent Immobilization of Protein Ligands for Affinity Chromatography." 2001, Prolinx, Inc, Washington State, USA). It is anticipated that it should be relatively simple to link a phenylboronic acid functionality to a peptide mass tag according to this invention to generate capture reagents that can be captured by selective chemical reactions. The use of this sort of chemistry would not be directly compatible with biomolecules bearing vicinal cis-diol-containing sugars, however these sorts of sugars could be blocked with phenylboronic acid or related reagents prior to reaction with boronic acid derivitised peptide mass tag reagents.

Mass Spec Sensitivity Enhancing Groups and Mass Differentiation

In preferred embodiments of aspects of this invention the peptide mass tags comprise Sensitivity Enhancing Groups. These Sensitivity Enhancing Groups can enhance the intensity in MS mode and the intensity of the mass marker or its fragments in MS/MS or MS/MS/MS mode. Suitable sensitivity enhancing groups are disclosed in WO 02/099435, WO 03/087839 and WO 2005/012914. Guanidino and tertiary amino groups are especially useful to enhance the MS/MS and MS/MS/MS intensity of the mass marker.

Various other methods for derivatising peptides have been also been developed. These include the use of quaternary ammonium derivatives, quaternary phosphonium derivatives and pyridyl derivatives for positive ion mass spectrometry. Halogenated compounds, particularly halogenated aromatic compounds are well known electrophores, i.e. they pick up thermal electrons very easily. A variety of derivatisation reagents based on fluorinated aromatic compounds (Bian N. et al., Rapid Commun Mass Spectrom 11(16): 1781-1784, "Detection via laser desorption and mass spectrometry of multiplex electrophore-labelled albumin." 1997) have been developed for electron capture detection, which is a highly sensitive ionisation and detection process that can be used with negative ion mass spectrometry (Abdel-Baly S. & Giese R. W., Anal Chem 63(24):2986-2989, "Gas chromatography/electron capture negative-ion mass spectrometry at the zeptomole level." 1991). A fluorinated aromatic group could also be used as a sensitivity enhancing group. Aromatic sulphonic acids have also been used for improving sensitivity in negative ion mass spectrometry.

Each type of Sensitivity Enhancing Group has different benefits, which depend on the method of ionisation used and on the methods of mass analysis used. The mechanism by which sensitivity is enhanced may also be different for each type of group. Some derivitisation methods increase basicity and thus promote protonation and charge localisation, while other methods increase surface activity of the tagged peptides, which improves sensitivity in surface desorption techniques like Matrix Assisted Laser Desorption Ionisation (MALDI) and Fast Atom Bombardment (FAB). Methods by which appropriate Sensitivity Enhancing Groups may be selected in order to enable higher MS mode sensitivity are disclosed in WO 02/099435, WO 03/087839 and WO 2005/012914. Negative ion mass spectrometry is often more sensitive because there is less background noise. Charge derivitisation can also change the fragmentation products of derivatised peptides, when collision induced dissociation is used. In particular some derivatisation techniques simplify fragmentation patterns, which is highly advantageous. The choice of Sensitivity Enhancing Group is determined by the mass spectrometric techniques that will be employed (for a review see Roth et al., Mass Spectrometry Reviews 17:255-274, "Charge derivatisation of peptides for analysis by mass spectrometry", 1998). For the purposes of this invention all of the known derivatisation techniques could be used with the peptide mass tags of this invention. The published protocols could be used without modification to derivitise the peptide mass tags of this invention after solid phase peptide synthesis or the protocols could be readily adapted for use during solid phase synthesis if desired.

Analysis of Peptides by Mass Spectrometry

The essential features of a mass spectrometer are as follows:

Inlet System→Ion Source→Mass Analyser→Ion Detector→Data Capture System

There are preferred inlet systems, ion sources and mass analysers for the purposes of analysing peptides.

Inlet Systems

In the second aspect of this invention a chromatographic or electrophoretic separation is preferred to reduce the complexity of the sample prior to analysis by mass spectrometry. A variety of mass spectrometry techniques are compatible with separation techologies particularly capillary zone electrophoresis and High Performance Liquid Chromatography (HPLC). Typical couplings include online HPLC-ESI or offline HPLC-MALDI.

Ionisation Techniques

For many biological mass spectrometry applications so called 'soft' ionisation techniques are used. These allow large molecules such as proteins and nucleic acids to be ionised essentially intact. A number of techniques are appropriate for use with this invention including but not limited to Electrospray Ionisation Mass Spectrometry (ESI-MS), Fast Atom Bombardment (FAB), Matrix Assisted Laser Desorption Ionisation Mass Spectrometry (MALDI MS) and Atmospheric Pressure Chemical Ionisation Mass Spectrometry (APCI-MS).

Electrospray Ionisation

Electrospray ionisation requires that the dilute solution of the analyte molecule is 'atomised' into the spectrometer, i.e. injected as a fine spray. The solution is, for example, sprayed from the tip of a charged needle in a stream of dry nitrogen and an electrostatic field. The mechanism of ionisation is not fully understood but is thought to work broadly as follows. In a stream of nitrogen the solvent is evaporated. With a small droplet, this results in concentration of the analyte molecule. Given that most biomolecules have a net charge this increases the electrostatic repulsion of the dissolved molecule. As evaporation continues this repulsion ultimately becomes greater than the surface tension of the droplet and the droplet disintegrates into smaller droplets. This process is sometimes referred to as a 'Coulombic explosion'. The electrostatic field helps to further overcome the surface tension of the droplets and assists in the spraying process. The evaporation continues from the smaller droplets which, in turn, explode iteratively until essentially the biomolecules are in the vapour phase, as is all the solvent. This technique is of particular importance in the use of mass labels in that the technique imparts a relatively small amount of energy to ions in the ionisation process and the energy distribution within a population tends to fall in a narrower range when compared with other techniques. The ions are accelerated out of the ionisation chamber by the use of electric fields that are set up by appropriately positioned electrodes. The polarity of the fields may be altered to extract either negative or positive ions. The potential difference between these electrodes determines whether positive or negative ions pass into the mass analyser and also the kinetic energy with which these ions enter the mass spectrometer. This is of significance when considering fragmentation of ions in the mass spectrometer. The more energy imparted to a population of ions the more likely it is that fragmentation will occur through collision of analyte molecules with the bath gas present in the source. By adjusting the electric field used to accelerate ions from the ionisation chamber it is possible to control the fragmentation of ions. This is advantageous when fragmentation of ions is to be used as a means of removing tags from a labelled biomolecule. Electrospray ionisation is particularly advantageous as it can be used in-line with liquid chromatography, referred to as Liquid Chromatography Mass Spectrometry (LC-MS).

Matrix Assisted Laser Desorption Ionisation (MALDI)

MALDI requires that the biomolecule solution be embedded in a large molar excess of a photo-excitable 'matrix'. The application of laser light of the appropriate frequency results in the excitation of the matrix which in turn leads to rapid evaporation of the matrix along with its entrapped biomolecule. Although the precise ionisation mechanism is not completely understood, it is believed that the biomolecule gives rise to protonated forms of the biomolecule which can be detected by positive ion mass spectrometry, particularly by Time-Of-Flight (TOF) mass spectrometry. Negative ion mass spectrometry is also possible by MALDI TOF. This technique imparts a significant quantity of translational energy to ions, but tends not to induce excessive fragmentation despite this. Fragmentation can be controlled in MALDI both by the accelerating voltages and the choice of the matrix.

Fast Atom Bombardment

Fast Atom Bombardment (FAB) has come to describe a number of techniques for vaporising and ionising relatively involatile molecules. In these techniques a sample is desorbed from a surface by collision of the sample with a high energy beam of xenon atoms or caesium ions. The sample is coated onto a surface with a simple matrix, typically a non volatile material, e.g. m-nitrobenzyl alcohol (NBA) or glycerol. FAB techniques are also compatible with liquid phase inlet systems—the liquid eluting from a capillary electrophoresis inlet or a high pressure liquid chromatography system pass through a frit, essentially coating the surface of the frit with analyte solution which can be ionised from the frit surface by atom bombardment.

Mass Analysers

Fragmentation of peptides by collision induced dissociation is used in this invention to identify tags on proteins. Various mass analyser geometries may be used to fragment peptides and to determine the mass of the fragments.

MS/MS and MS$^n$ Analysis of Peptides

Tandem mass spectrometers allow ions with a pre-determined mass-to-charge ratio to be selected and fragmented by collision induced dissociation (CID). The fragments can then be detected providing structural information about the selected ion. When peptides are analysed by CID in a tandem mass spectrometer, characteristic cleavage patterns are observed, which allow the sequence of the peptide to be determined. Natural peptides typically fragment randomly at the amide bonds of the peptide backbone to give series of ions that are characteristic of the peptide. CID fragment series are denoted $a_n$, $b_n$, $c_n$, etc. for cleavage at the $n^{th}$ peptide bond where the charge of the ion is retained on the N-terminal fragment of the ion. Similarly, fragment series are denoted $x_n$, $y_n$, $z_n$, etc. where the charge is retained on the C-terminal fragment of the ion.

A typical tandem mass spectrometer geometry is a triple quadrupole which comprises two quadrupole mass analysers separated by a collision chamber, also a quadrupole. This collision quadrupole acts as an ion guide between the two mass analyser quadruples. A gas can be introduced into the collision quadrupole to allow collision with the ion stream from the first mass analyser. The first mass analyser selects ions on the basis of their mass/charge ration which pass through the collision cell where they fragment. The fragment ions are separated and detected in the third quadrupole. Importantly for the present invention, ions can be selected in the third mass analyser on the basis of their mass/charge ratio, passed through to a further collision cell for fragmentation, and the fragment ions separated and detected in a further mass analyser.

The present invention enables the detection of known analytes in a very sensitive way in multiple reaction monitoring (MRM) experiments using a triple quadrupole instrument. MRM is designed for obtaining maximum sensitivity for detection of target compounds. This type of mass spectrometric experiment is widely used in detecting and quantifying drugs and drug metabolites in the pharmaceutical industry. Knowing the mass and structure of a target molecule, it is possible to predict the precursor m/z and a fragment m/z (MRM transition) for the target molecule. These MRM experiments can be used to screen for such analytes.

Induced cleavage can be performed in geometries other than tandem analysers. Ion trap mass spectrometers can promote fragmentation through introduction of a gas into the trap itself with which trapped ions will collide. Ion traps generally contain a bath gas, such as helium. Similarly photon induced fragmentation could be applied to trapped ions. Another favourable geometry is a Quadrupole/Orthogonal Time of Flight tandem instrument where in MS/MS mode the static passage through the quadrupole is coupled to the greater sensitivity of a reflectron TOF mass analyser to identify the products of fragmentation.

Conventional 'sector' instruments are another common geometry used in tandem mass spectrometry. A sector mass analyser comprises two separate 'sectors', an electric sector which focuses an ion beam leaving a source into a stream of ions with the same kinetic energy using electric fields. The magnetic sector separates the ions on the basis of their mass to generate a spectrum at a detector. For tandem mass spectrometry a two sector mass analyser of this kind can be used where the electric sector provide the first mass analyser stage, the magnetic sector provides the second mass analyser, with a collision cell placed between the two sectors. Two complete sector mass analysers separated by a collision cell can also be used for analysis of mass tagged peptides.

Ion Trap mass analysers are related to the quadrupole mass analysers. The ion trap generally has a 3 electrode construction—a cylindrical electrode with 'cap' electrodes at each end forming a cavity. A sinusoidal radio frequency potential is applied to the cylindrical electrode while the cap electrodes are biased with DC or AC potentials. Ions injected into the cavity are constrained to a stable circular trajectory by the oscillating electric field of the cylindrical electrode. However, for a given amplitude of the oscillating potential, certain ions will have an unstable trajectory and will be ejected from the trap. A sample of ions injected into the trap can be sequentially ejected from the trap according to their mass/charge ratio by altering the oscillating radio frequency potential. The ejected ions can then be detected allowing a mass spectrum to be produced.

Ion traps are generally operated with a small quantity of a 'bath gas', such as helium, present in the ion trap cavity. This increases both the resolution and the sensitivity of the device as the ions entering the trap are essentially cooled to the ambient temperature of the bath gas through collision with the bath gas. Collisions both decelerate ions when a sample is introduced into the trap and dampen the amplitude and velocity of ion trajectories keeping them nearer the centre of the trap.

Ion traps can mimic tandem mass spectrometer geometries, in fact they can mimic multiple mass spectrometer geometries allowing complex analyses of trapped ions. A single mass species from a sample can be retained in a trap, i.e. all other species can be ejected and then the retained species can be carefully excited by super-imposing a second oscillating frequency on the first. The excited ions will then collide with the bath gas and will fragment if sufficiently excited. The fragments can then be analysed further. It is possible to retain a fragment ion for further analysis by ejecting other ions and then exciting the fragment ion to fragment. This process can be repeated for as long as sufficient sample exists to permit further analysis. It should be noted that these instruments generally retain a high proportion of fragment ions after induced fragmentation. These instruments and FTICR mass spectrometers (discussed below) represent a form of temporally resolved tandem mass spectrometry rather than spatially resolved tandem mass spectrometry which is found in linear mass spectrometers.

Fourier Transform Ion Cyclotron Resonance Mass Spectrometry (FTICR MS)

FTICR mass spectrometry has similar features to ion traps in that a sample of ions is retained within a cavity but in FTICR MS the ions are trapped in a high vacuum chamber by crossed electric and magnetic fields. The electric field is generated by a pair of plate electrodes that form two sides of a box. The box is contained in the field of a superconducting magnet which in conjunction with the two plates, the trapping plates, constrain injected ions to a circular trajectory between the trapping plates, perpendicular to the applied magnetic field. The ions are excited to larger orbits by applying a radio-frequency pulse to two 'transmitter plates' which form two further opposing sides of the box. The cycloidal motion of the ions generate corresponding electric fields in the remaining two opposing sides of the box which comprise the 'receiver plates'. The excitation pulses excite ions to larger orbits which decay as the coherent motions of the ions is lost through collisions. The corresponding signals detected by the receiver plates are converted to a mass spectrum by Fourier Transform (FT) analysis.

For induced fragmentation experiments these instruments can perform in a similar manner to an ion trap—all ions except a single species of interest can be ejected from the trap. A collision gas can be introduced into the trap and fragmentation can be induced. The fragment ions can be subsequently analysed. Generally fragmentation products and bath gas combine to give poor resolution if analysed by FT analysis of signals detected by the 'receiver plates', however the fragment ions can be ejected from the cavity and analysed in a tandem configuration with a quadrupole, for example.

Separation of Labelled Peptides by Chromatography or Electrophoresis

In one embodiment of the invention, labelled biomolecules are subjected to a chromatographic separation prior to analysis by mass spectrometry. This is preferably High Performance Liquid Chromatography (HPLC) which can be coupled directly to a mass spectrometer for in-line analysis of the peptides as they elute from the chromatographic column. A variety of separation techniques may be performed by HPLC but reverse phase chromatography is a popular method for the separation of peptides prior to mass spectrometry. Capillary zone electrophoresis is another separation method that may be coupled directly to a mass spectrometer for automatic analysis of eluting samples. These and other fractionation techniques may be applied to reduce the complexity of a mixture of biomolecules prior to analysis by mass spectrometry.

Applications of the Invention

Labelling Peptides and Polypeptides and Analysis by LC-MS-MS-MS

In preferred embodiments of the second aspect of this invention, the tags are used for the analysis of mixtures of peptides by liquid chromatography triple mass spectrometry (LC-MS-MS-MS). The use of the mass labels of this invention will now be discussed in the context of the analysis of peptides. Mass labels such as those in the figures may be used to label peptides. If the reactive functionality on these compounds is an N-hydroxysuccinimide ester then the tags will be reactive with free amino groups such as alpha-amino groups and epsilon amino groups in lysine.

After attachment of the tags, the labelled peptides will have a mass that is shifted by the mass of the tag. The mass of the peptide may be sufficient to identify the source protein. In this case only the tag needs to be detected which can be achieved by selected reaction monitoring with a triple quadrupole, discussed in more detail below. Briefly, the first quadrupole of the triple quadrupole is set to let through ions whose mass-to-charge ratio corresponds to that of the peptide of interest, adjusted for the mass of the marker. The selected ions are then subjected to collision induced dissociation (CID) in the second quadrupole. Under the sort of conditions used in the analysis of peptides the ions will fragment mostly at the amide bonds in the molecule. The markers in FIG. 1 has an amide bond, which releases the N-terminal portion of the tag on cleavage. Although the tags all have the same mass, the terminal portion is different between groups of labels because of differences in the substituents on either side of the amide bond. Thus groups of mass labels can be distinguished from each other. The presence of the marker fragment associated with an ion of a specific mass should confirm that the ion was a peptide and the relative peak heights of the tags from different samples will give information about the relative quantities of the peptides in their samples. If the mass is not sufficient to identify a peptide, either because a number of terminal peptides in the sample have the same terminal mass or because the peptide is not known, then sequence information may be determined by analysis of the complete CID spectrum. The peptide fragmentation peaks can be used to identify the peptides while the mass tag peaks give information about the relative quantities of the peptides.

The analysis of proteins by tandem mass spectrometry, particularly mixtures of peptides, is complicated by the 'noisiness' of the spectra obtained. Peptides isolated from biological samples are often contaminated with buffering reagents, denaturants and detergents, all of which introduce peaks into the mass spectrum. As a result, there are often more contamination peaks in the spectrum than peptide peaks and identifying peaks that correspond to peptides is major problem, especially with small samples of proteins that are difficult to isolate. As a result various methods are used to determine which peaks correspond to peptides before detailed CID analysis is performed. Triple quadrupole based instruments permit 'precursor ion scanning' (see Wilm M. et al., Anal Chem 68(3):527-33, "Parent ion scans of unseparated peptide mixtures." (1996)). The triple quadrupole is operated in 'single reaction monitoring' mode, in which the first quadrupole scans over the full mass range and each gated ion is subjected to CID in the second quadrupole. The third quadrupole is set to detect only one specific fragment ion, which is usually a characteristic fragment ion from a peptide such as immonium ions. The presence of phosphate groups can also be detected using this sort of technique.

Besides precursor ion scanning, selected reaction monitoring (SRM) can be used to obtain maximum sensitivity for target analytes. SRM is performed by specifying the parent m/z of the compound for MS/MS fragmentation and then specifically monitoring for a single fragment ion. Together with the labels described above it is possible to analyze a number of samples together in one SRM experiment in which the mass marker moiety is monitored as the fragment ion. The additional MS/MS/MS step allows quantification of the array of samples via the fragments of the mass marker moiety.

Multiple reaction monitoring (MRM) uses a similar experimental methodology but more than one transition. These highly sensitive SRM and MRM experiments can be used to trigger dependent acquisition of product ion scans (MS/MS) using a hybrid quadrupole-linear ion trap instrument. Such an instrument also allows an additional MS step (to give MS/MS/MS or $MS^3$), in contrast to conventional triple quadrupole instruments which are limited to MS/MS. In proteomics applications this is very useful for the statistical validation of peptide or protein quantitation for a high number of species. The combination of the described tags together with highly sensitive MRM scans and additionally an $MS^3$ scan provides the validation data of a high number of species in a single run.

By labelling peptides with the mass labels of this invention, a novel form of precursor ion scanning may be envisaged in which peptide peaks are identified by the presence of fragments corresponding to the mass labels of this invention after subjecting the labelled peptides to CID. In particular, the peptides isolated from each sample by the methods of this invention may be labelled with more than one tag. An equimolar mixture of a 'precursor ion scanning' tag which is used in all samples and a sample specific tag may be used to label the peptides in each sample. In this way changes in the level of peptides in different samples will not have an adverse effect on the identification of peptide peaks in a precursor ion scan.

Having identified and selected a peptide ion, it is subjected to CID. The CID spectra are often quite complex and determining which peaks in the CID spectrum correspond to meaningful peptide fragment series is a further problem in determining the sequence of a peptide by mass spectrometry. Shevchenko et al., Rapid Commun. Mass Spec. 11: 1015-1024 (1997) describe a further method, which involves treating proteins for analysis with trypsin in 1:1 $^{16}O/^{18}O$ water. The hydrolysis reaction results in two populations of peptides, the first whose terminal carboxyl contains $^{16}O$ and the second whose terminal carboxyl contains $^{18}O$. Thus for each peptide in the sample there should be a double peak of equal intensity for each peptide where the double peak is 2 Daltons apart. This is complicated slightly by intrinsic peptide isotope peaks but allows for automated scanning of the CID spectrum for doublets. The differences in mass between doublets can be determined to identify the amino acid by the two fragments differ. This method may be applicable with the methods of this invention.

Protein Expression Profiling

To understand the changes in a cancerous tissue, for example, requires an understanding of all of the molecular changes in that tissue, ideally relating these changes to normal tissue. To determine all of the molecular changes requires the ability to measure changes in gene expression, protein expression and ultimately metabolite changes. It is possible to compare the expression, between different tissue samples, of large numbers of genes simultaneously at the level of messenger RNA (mRNA) using microarray technology (see for example Iyer V. R. et al., Science 283(5398):83-87, "The transcriptional program in the response of human fibroblasts to serum." 1999), however mRNA levels do not correlate directly to the levels of protein in a tissue. To determine a protein expression profile for a tissue, 2-dimensional gel electrophoresis is widely used. Unfortunately, this technique is extremely laborious and it is difficult to compare two or more samples simultaneously on a 2-D gel due to the difficulty of achieving reproducibility. As discussed above peptides may be analysed effectively using the methods of this invention. The tags of this invention allow the same peptide from different samples to be identified using LC-MS-MS. In addition, the relative quantities of the same peptide in different samples may be determined. The ability to rapidly and sensitively determine the identity and relative quantities of peptides in a number of samples allows for expression profiling. Therefore it is an object of this invention to provide improved methods for comparative analysis of complex protein samples based on the selective isolation and labelling of peptides. Two published approaches for the global analysis of protein expression are discussed and various methods for the analysis of particular protein states, such as phospholylation and carbohydrate modification are also described below.

Terminal Peptide Isolation for Flobal Protein Expression Profiling

Isolation of N- or C-terminal peptides has been described as a method to determine a global expression profile of a protein sample. Isolation of terminal peptides ensures that at least one and only one peptide per protein is isolated thus ensuring that the complexity of the sample that is analysed does not have more components than the original sample. Reducing large polypeptides to shorter peptides makes the sample more amenable to analysis by mass spectrometry. Methods for isolating peptides from the termini of polypeptides are discussed in PCT/GB98/00201, PCT/GB99/03258.

The invention claimed is:

1. A set of mass labels, each mass label in the set comprising a mass marker moiety attached via a cleavable linker to a mass normalisation moiety, wherein when the linker is cleaved by dissociation in a mass spectrometer, each mass label is adapted to dissociate to form the mass marker moiety and the mass normalization moiety, each mass label in the set having a common mass; wherein
the set comprises a plurality of groups of mass labels, the mass of the mass marker moiety being the same for mass labels within a group, the mass of the mass marker moiety being different between groups;
the mass marker moiety is capable of fragmentation by collision induced dissociation in the mass spectrometer into two or more fragments; and
the mass of at least one fragment of the mass marker moiety differs between mass labels within a group such that each mass marker moiety of the mass labels within a group is distinguishable from one another by mass spectrometry, wherein one or more mass labels in the set comprises one or more isotopic labels and wherein the isotopic label comprises $^2H$, $^{13}C$, $^{15}N$ or $^{18}O$.

2. A set of mass labels according to claim 1, wherein each mass label in the set comprises an isotopic label, the position of the isotopic label varying between mass labels in the set.

3. A set of mass labels according to claim 1, wherein each mass label in the set comprises two or more isotopic labels, each mass label in the set comprising an equal number of isotopic labels, the position of the labels varying between mass labels in the set.

4. A set of mass labels according to claim 1, wherein in a group of mass labels, each mass marker moiety comprises an equal number of isotopic labels.

5. A set of mass labels according to claim 1, wherein in a group of mass labels, each mass normalization moiety comprises an equal number of isotopic labels.

6. A set of mass labels according to claim 1, wherein in a group of mass labels in the set, the mass marker moiety of each mass label comprises at least one isotopic label, the position of at least one isotopic label varying between mass labels in the group.

7. A set of mass labels according to claim 1, wherein each mass label in a group comprises an isotopic label at a different position in the mass marker moiety, such that the isotopic label is comprised in a different fragment in each mass label in the group.

8. A set of mass labels according to claim 1, wherein each mass label in a group comprises two or more isotopic labels, the position of at least one isotopic label varying between mass labels in the group, such that at least one isotopic label is comprised in a different fragment of the mass marker moiety in each mass label in the group.

9. A set of mass labels, each mass label in the set comprising a mass marker moiety attached via a cleavable linker to a mass normalisation moiety, wherein when the linker is cleaved by dissociation in a mass spectrometer, each mass label is adapted to dissociate to form the mass marker moiety and the mass normalization moiety, each mass label in the set having a common mass; wherein
the set comprises a plurality of groups of mass labels, the mass of the mass marker moiety being the same for mass labels within a group, the mass of the mass marker moiety being different between groups;
the mass marker moiety is capable of fragmentation by collision induced dissociation in the mass spectrometer into two or more fragments; and
the mass of at least one fragment of the mass marker moiety differs between mass labels within a group such that each mass marker moiety of the mass labels within a group is distinguishable from one another by mass spectrometry, wherein one or more mass labels in the set comprises one or more isotopic labels and wherein the isotopic label comprises $^2H$, $^{13}C$, $^{15}N$ or $^{18}O$ and, wherein each mass label in a group comprises a mass marker moiety which is the same chemical species, each mass label in the group comprising an isotopic marker at a different position in the mass marker moiety.

10. A set of mass labels, each mass label in the set comprising a mass marker moiety attached via a cleavable linker to a mass normalisation moiety, wherein when the linker is cleaved by dissociation in a mass spectrometer, each mass label is adapted to dissociate to form the mass marker moiety and the mass normalization moiety, each mass label in the set having a common mass; wherein
the set comprises a plurality of groups of mass labels, the mass of the mass marker moiety being the same for mass labels within a group, the mass of the mass marker moiety being different between groups;
the mass marker moiety is capable of fragmentation by collision induced dissociation in the mass spectrometer into two or more fragments; and
the mass of at least one fragment of the mass marker moiety differs between mass labels within a group such that each mass marker moiety of the mass labels within a group is distinguishable from one another by mass spectrometry, wherein one or more mass labels in the set comprises one or more isotopic labels and wherein the isotopic label comprises $^2H$, $^{13}C$, $^{15}N$ or $^{18}O$, the position of at least one isotopic label varying between mass labels in the group, such that at least one isotopic label is comprised in a different fragment of the mass marker moiety in each mass label in the group and, wherein each mass label in the set is the same chemical species, each mass label in the set comprises two or more isotopic labels, each mass label in the set comprises an equal number of isotopic labels, each mass label in a group comprises a first number of isotopic markers in the mass marker moiety and a second number of isotopic markers in the mass normalisation moiety, and the first number and the second number differs between groups.

11. A set of mass labels according to claim 1, wherein the mass of the mass normalisation moiety is equal for mass labels within a group and differs between groups.

12. An array of mass labels, comprising a plurality of sets of mass labels according to claim 1, wherein the common mass of the mass labels is different for each set.

13. A set of labelled analytes, wherein each labelled analyte in the set comprises an analyte attached to a different mass label or a different combination of mass labels from a set or array of mass labels as defined in claim 1.

14. A set of labelled analytes according to claim 13, wherein the set of labelled analytes thereby comprises a set or array of mass labels as defined in claim 1.

15. A set of labelled analytes according to claim 13, wherein each analyte in the set is different or is derived from a different sample.

16. A set of two or more labelled probes, wherein each labeled probe in the set comprises a probe attached to a different mass label or a different combination of mass labels, from a set or array of mass labels as defined in claim 1.

17. A set of labelled analytes or labelled probes according to claim 13, wherein each analyte or probe comprises a biomolecule.

18. A set of analytes or probes according to claim 17, wherein the biomolecule is selected from a DNA, an RNA, an oligonucleotide, a nucleic acid base, a protein and/or an amino acid.

19. A method of analysis, which method comprises detecting an analyte by identifying by mass spectrometry a mass label or a combination of mass labels relatable to the analyte, wherein the mass label is a mass label from a set or array of mass labels as defined in claim 1.

20. A method according to claim 19, wherein the mass labels employed are labels comprising an affinity capture ligand, and labelled analytes are separated from unlabelled analytes by capturing the affinity capture ligand with a counter ligand.

21. A method according to claim 19, in which two or more analytes are detected by simultaneously identifying their mass labels or combinations of mass labels by mass spectrometry.

22. A method according to claim 19, wherein each analyte is identified by a unique combination of mass labels from a set or array of mass labels, each combination being distinguished by the presence and absence of each mass label in the set or array and/or the quantity of each mass label.

23. A method according to claim 19 for identifying two or more analytes, wherein the analytes are separated according to their mass, prior to detecting their mass labels by mass spectrometry.

24. A method according to claim 20, wherein separation is carried out by a chromatographic or electrophoretic method.

25. A method according to claim 19, wherein the mass spectrometer employed to detect the mass label comprises one or more mass analysers, which mass analysers are capable of allowing ions of a particular mass, or range of masses, to pass through for detection and/or are capable of causing ions to dissociate.

26. A method according to claim 25, wherein ions of a particular mass or range of masses specific to one or more known mass labels are selected using the mass analyser, the selected ions are dissociated, and the dissociation products are detected to identify ion patterns indicative of the selected mass labels.

27. A method according to claim 25, wherein the mass spectrometer comprises three or more quadrupole mass analysers.

28. A method according to claim 25, wherein the mass spectrometer comprises two quadrupole mass analysers and an ion trap mass analyser.

29. A method according to claim 27, wherein a first mass analyser is used to select ions of a particular mass or mass range, a second mass analyser is used to dissociate the selected ions, and a third mass analyser is used to detect resulting ions.

30. A method according to claim 19, which method comprises:
   (a) contacting one or more analytes with a set of labelled probes, wherein each labelled probe in the set comprises a probe attached to a different mass label or a different combination o mass labels,
   (b) identifying an analyte, by detecting a probe relatable to that analyte.

31. A method according to claim 30, wherein the mass label is cleaved from the probe prior to detecting the mass label by mass spectrometry.

32. A method according to claim 30, which method comprises contacting one or more nucleic acids with a set of hybridisation probes.

33. A method of mass spectrometric analysis, comprising:
   (a) detecting a set of mass labels as defined in claim 1 in a mass spectrometer;
   (b) dissociating the mass labels in the mass spectrometer, to release the mass marker moieties from the mass normalisation moieties;
   (c) detecting the mass marker moieties in the mass spectrometer;
   (f) fragmenting the mass marker moieties in the mass spectrometer to produce two or more fragments from each mass marker moiety; and
   (f) detecting the fragments.

34. A method according to claim 33, wherein the mass labels are comprised in a set of labelled analytes as defined in claim 13.

35. A method according to claim 19, which comprises a multiple reaction monitoring experiment.

36. A set of mass labels according to claim 1 wherein the linker is adapted to be easily broken in the mass spectrometer.

* * * * *